United States Patent [19]
Parab et al.

[11] Patent Number: 6,019,988
[45] Date of Patent: *Feb. 1, 2000

[54] METHODS AND COMPOSITIONS FOR ENHANCING SKIN PERMEATION OF DRUGS USING PERMEATION ENHANCERS, WHEN DRUGS AND/OR PERMEATION ENHANCERS ARE UNSTABLE IN COMBINATION DURING LONG-TERM STORAGE

[75] Inventors: Prakash Parab, Williamsville; Cheng Der Tony Yu; Bhiku Patel, both of Amherst, all of N.Y.

[73] Assignee: Bristol-Myers Squibb Company, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/751,293

[22] Filed: Nov. 18, 1996

[51] Int. Cl.$^7$ ...................................................... A61K 9/70
[52] U.S. Cl. ......................... 424/400; 424/445; 424/448; 424/449; 424/443; 424/402; 424/404
[58] Field of Search ..................................... 424/400, 445, 424/448, 449, 402, 404, 443; 514/170, 946, 873, 947, 859

[56] References Cited

U.S. PATENT DOCUMENTS

| | | | |
|---|---|---|---|
| 4,379,454 | 4/1983 | Campbell et al. | 604/897 |
| 4,497,794 | 2/1985 | Klein et al. | 424/81 |
| 4,592,487 | 6/1986 | Simon et al. | 222/94 |
| 4,666,441 | 5/1987 | Andriola et al. | 604/897 |
| 4,823,985 | 4/1989 | Grollier et al. | 222/1 |
| 4,956,171 | 9/1990 | Chang et al. | 424/449 |
| 5,028,431 | 7/1991 | Franz et al. | 424/449 |
| 5,156,846 | 10/1992 | Petersen et al. | 424/401 |
| 5,223,262 | 6/1993 | Kim et al. | 424/448 |
| 5,326,566 | 7/1994 | Parab et al. | 424/401 |
| 5,422,119 | 6/1995 | Casper | 424/449 |
| 5,436,369 | 7/1995 | Bronson et al. | 562/495 |
| 5,538,732 | 7/1996 | Smith et al. | 424/402 |

FOREIGN PATENT DOCUMENTS

| | | |
|---|---|---|
| 4435805 | 4/1996 | Germany . |
| 92/09266 | 6/1992 | WIPO . |
| 92/17183 | 10/1992 | WIPO . |

*Primary Examiner*—S. Mark Clardy
*Assistant Examiner*—Kathryne E. Shelborne
*Attorney, Agent, or Firm*—Morton S. Simon; Charles J. Zeller

[57] ABSTRACT

The invention provides methods and means for enhancing the epidermal, transdermal and dermal permeation of a topically applied pharmacologically active agent (e.g., a drug or medicament) which has a low rate of skin penetration in the absence of a permeation enhancer and which is unstable and degrades during long-term storage with particular permeation enhancers. Also provided by the invention are methods and means to increase the skin penetration of a pharmacologically active agent which has a normally low rate of skin permeation and causes the instability and degradation of a permeation enhancer with which it is combined over a long period of time. Provided by the invention are at least one first composition containing a drug, a pharmaceutically acceptable salt, chemical derivative or formulation thereof, in a dermatologically acceptable vehicle, and at least one second composition containing a permeation enhancer in an acceptable vehicle. The compositions are physically separated until application to a body or skin surface and are topically applied, either at the same time, or sequentially within a short time of each other, and mixed or blended to form a final active composition, preferably on the skin. In addition, a premixture of the compositions can be made and applied to the skin in accordance with the invention. The invention allows a therapeutically effective amount of drug to be delivered into the skin and systemic circulation and provides significant enhancement of a drug's otherwise low level of skin permeation by the action of permeation enhancer in the active composition at the point of use.

46 Claims, 13 Drawing Sheets

(A)—GEAHLENE BASE (n=8)
(B)—DUAL SYSTEM W/SLS (n=8)
(C)—DUAL SYSTEM W/DECYL METHYL SULFOXIDE (n=8)
(D)—DUAL SYSTEM W/d-LIMONENE (n=8)
(E)—DUAL SYSTEM W/MENTHONE (n=8)

(A)—GEAHLENE BASE
(B)—DUAL SYSTEM W/SLS
(C)—DUAL SYSTEM W/DECYL METHYL SULFOXIDE
(D)—DUAL SYSTEM W/d-LIMONENE
(E)—DUAL SYSTEM W/MENTHONE (A)-GEAHLENE BASE (n=7)
(B)-DUAL SYSTEM W/SLS (n=8)
(C)-DUAL SYSTEM W/DECYL METHYL SULFOXIDE (n=8)
(D)-DUAL SYSTEM W/d-LIMONENE (n=8)
(E)-DUAL SYSTEM W/MENTHONE (n=8)

METHODS AND COMPOSITIONS FOR ENHANCING SKIN PERMEATION OF DRUGS USING PERMEATION ENHANCERS, WHEN DRUGS AND/OR PERMEATION ENHANCERS ARE UNSTABLE IN COMBINATION DURING LONG-TERM STORAGE

FIELD OF THE INVENTION

The present invention relates generally to the field of enhancement of skin permeation of a pharmacologically or therapeutically active compound, which is preferably topically or transdermally applied to the skin. In particular, the invention relates to enhancement and control of epidermal, transdermal, and dermal penetration of a variety of topically applied drugs, which normally exhibit a low rate of skin permeation or penetration, and which are incompatible for long-term formulation and storage with permeation enhancers, due to instability and degradation of drug when combined with one or more permeation enhancers, or due to instability and degradation of the permeation enhancer when combined with drug, over a long period of time.

BACKGROUND OF THE INVENTION

The transdermal route of administration of therapeutically active drugs has been used by investigators to deliver the drugs into the systemic circulation of mammals, including humans. However, despite the development of various means for the transdermal delivery of drugs, the skin of humans and other animals provides an excellent barrier to the penetration of chemical substances that are exogenously applied. The outermost layer of skin, the stratum corneum, offers maximum resistance to penetration, while the lower skin layers are relatively more permeable. For the proper treatment of skin disorders and diseases, it is important that the pharmacologically active agent penetrate the stratum corneum and be made available at appropriate concentrations at the site of action, which can be the stratum corneum, the viable epidermis, the epidermis-dermis junction, the dermis per se, or all of the aforementioned layers of the skin, depending upon the type of skin disorder or skin disease condition.

Various dermal effective pharmacological agents are known which can provide beneficial effects when applied topically to the skin to treat surface or subsurface diseases or for creating skin conditions which protect the skin from external factors. Other pharmacological agents are also known which can provide beneficial effects when absorbed into the systemic circulation. Thus, it is possible to have a systemic effect through topical application of a composition. The topical delivery of systemically effective pharmacological agents can be of significant value in cases where drugs produce gastric problems, are not well absorbed when given orally, or are rapidly metabolized in the liver, e.g. the "first pass" effect. In such cases, the use of topical delivery can give a systemic response at lower dosage than required orally. Topical delivery also avoids the disadvantages present in the intravenous route of administration, which might otherwise be required in order to achieve effective blood levels at reasonable dosage amounts. In addition, dermatological agents can be made more beneficial by enhancing their penetration through the protective layer of the skin in accordance with the present invention.

In certain dermatological conditions or pathologies, such as ichthyosis, callus, or plaque psoriasis, the stratum corneum is thicker and therefore can provide a significantly greater barrier to penetration of a drug, thus reducing its efficacy. Moreover, recent studies have shown that with increasing age, a person's skin becomes more resistant to penetration by water soluble drugs. In a few disease conditions, for example, psoriasis, the stratum corneum is not intact and hence is more permeable than that of normal skin. As the disease or condition improves, there is restructuring of the barrier, and resistance to the permeation of the therapeutically active agent will increase.

The use of penetration or permeation enhancers has been found to be critical to achieve a consistent supply of a therapeutically active ingredient at the site of action during the treatment of skin diseases. For example, as described in U.S. Pat. No. 5,326,566, a composition of such systemically effective pharmacological agents in combination with dibutyl adipate, or a mixture of dibutyl adipate and isopropyl myristate, can greatly enhance the rate of penetration of agents through the skin and can increase the amount absorbed into the systemic circulation. Although a variety of permeation enhancing agents have been used for enhancing the absorption of therapeutic agents into and through the skin, serious problems can arise when permeation enhancers are incompatible with a given drug over a long time period, thereby resulting in drug instability and degradation when the enhancers and the drug are co-formulated into a pharmaceutically acceptable composition for use in warm-blooded mammals, including humans. As a consequence, the practitioner in the art is hampered by an inability to employ certain permeation enhancers for increasing the skin permeation of a drug, if the permeation enhancer and the drug cannot be mixed and stored together without the drug becoming unstable over time and degrading to produce unwanted and potentially harmful byproducts. In addition to the formation of such drug breakdown products, there is also a risk of administering these breakdown products into the circulation of a warm-blooded mammal, including human patients, along with the active drug. Thus, if a drug has demonstrated efficacy in treating a particular affliction of the skin and related tissues, but has a low rate of skin permeation and is unstable for long-term formulation with and storage in permeation enhancing compositions, the utility of such drugs for medical and clinical development and for personal use is greatly diminished, if not abolished. Accordingly, in view of the foregoing, and because, upon storage, the permeation enhancer degrades the drug in question, or vice versa, one skilled in the art would be led away from using the permeation enhancer with particular drugs with particular permeation enhancers, and vice versa.

Moreover, in certain instances, the permeation enhancer may be incompatible with a drug and/or the composition containing the drug over a long time period, thereby resulting in instability of the permeation enhancer and its degradation when the permeation enhancer and the drug are co-formulated into a pharmaceutically acceptable composition for use in warmblooded mammals, including humans. As a consequence, one skilled in the art is hampered by an inability to employ certain permeation enhancers for increasing skin permeation of a drug, if the permeation enhancer and the drug cannot be mixed and stored together in a pharmaceutically acceptable composition without the permeation enhancer becoming unstable over time and degrading to produce unwanted and potentially harmful products.

Accordingly, the present invention allows drugs having a generally low rate of skin permeation to be used with a permeation enhancer to significantly improve the rate of skin penetration of the drug after topical application by providing separate formulations of the drug, in an appropriate pharmacological vehicle, and of the permeation enhancer, preferably in an appropriate pharmacological vehicle, wherein the drug and the permeation enhancer are combined and mixed at the site of application on the skin only at or shortly before the time of topical application on the skin.

The present invention also provides a solution to the instability problem encountered when a drug having a low rate of skin permeation is used with a permeation enhancer which does not have long-term stability in the composition containing the drug. The invention allows a drug having a low rate of skin permeation to be used with a permeation enhancer having instability with the drug and/or a composition containing the drug to improve significantly the rate of skin permeation of the drug after topical application on the skin by providing three separate formulations: one of drug, another of permeation enhancer, and yet another of a vehicle. The drug, permeation enhancer, and vehicle formulations are combined and mixed at the site of application only at or shortly before the time of application on the skin.

In certain instances a drug having a low rate of skin permeation and a permeation enhancer may be compatible with each other, but one or both may not have long-term stability in the vehicle for the drug. In such instances, the use of the present invention will significantly improve the skin permeation of the drug after its topical application by providing two separate formulations: one formulation containing the drug plus the permeation enhancer and the second containing vehicle. The formulation containing the drug and permeation enhancer and the formulation containing the vehicle is combined and mixed at the site of application only at or shortly before the time of application on the skin.

Thus, as a result of the present invention, the rate of skin penetration of a drug in the active composition is greatly enhanced over the penetration rate of the drug in the absence of enhancer. In addition, the present invention provides a solution to the aforementioned problems in the art by allowing those skilled in the art to utilize a permeation enhancer with a drug, regardless of a low penetration rate of the drug, or the incompatibility of the drug with particular permeation enhancers, or vice versa, after being combined therewith.

Grollier et al., U.S. Pat. No. 4,823,985, teaches the use of a dispensing assembly for at least two constituents used in hair coloration and having specified viscosities to enable the common dispensing of the constituents and the production of a composition on a site of application. Grollier et al. describe the preparation of cosmetic products for hair care and, unlike the present invention, are not concerned with the permeation-enhanced, transdermal delivery of a drug having a low permeation rate and an incompatibility with a permeation enhancing agent with which it is combined.

Petersen et al., U.S. Pat. No. 5,156,846, discloses a percutaneous drug delivery system and method which requires pretreating the skin with a skin permeation enhancer, which is an enzyme preparation, and occluding the area of the skin to which the skin permeation enhancing enzyme preparation is applied, removing the skin occlusion means, and applying a drug after rinsing the area. It is disclosed that the skin can again be occluded following application of the drug on the enzyme-pretreated site.

Y. Chang, U.S. Pat. No. 4,956,171, teaches a transdermal drug delivery system having a dual permeation enhancer in which the specific permeation enhancers are sucrose cocoate and methyl laurate. These two enhancers are required for use due to their ability to synergize for penetration enhancement. Unlike the present invention, the disclosure does not relate to a drug and/or permeation enhancer that are unstable during long-term storage with certain permeation enhancers and/or drugs, respectively, which may induce degradation of the drug and/or permeation enhancer, but which can also increase the permeation of the drug when the drug and enhancer are mixed on the skin at the point of use.

German Patent Application No. DE4435805-A1 discloses formation of an enzyme cream at the site of application from an enzyme containing anhydrous ointment base and an aqueous tenside containing oily emulsion (or a mixture of emulsifiers) which are packaged separately. The cream is disclosed to provide enzyme stability and maximum activity at the application site. This patent application deals with an incompatibility between an enzyme and an emulsion vehicle, with the purpose being to maintain enzyme activity at the site of application. This application does not involve or suggest a method and means to increase and enhance the permeation level of a drug which, in the absence of permeation enhancer, has a low level of skin permeation, but which is unstable in the presence of permeation enhancer.

Klein et al., U.S. Pat. No. 4,497,794, discloses a method and composition for the topical treatment of acne, which require the use of the drugs benzoyl peroxide and erythromycin, or derivatives thereof. The patent is not concerned with permeation enhancers and discloses that the two required drug components may be applied to the skin as a mixture or separately applied to the skin; however, unlike the present invention, peroxide, particularly benzoyl peroxide, synergizes with erythromycin. The patentees disclose that erythromycin and benzoyl peroxide, though chemically incompatible, were rendered stable by adding the surfactant, dioctyl sodium sulfosuccinate, to the disclosed benzoyl peroxide/erythromycin gel composition. By contrast, the present invention requires no additives to stabilize the permeation enhancer composition.

Campbell et al., U.S. Pat. No. 4,379,454, discloses a means for delivering to a defined area of skin a co-administered and controlled dosage of a drug and a percutaneous absorption enhancer, with particular regard to a dosage form and method for co-administering estradiol and ethanol percutaneously to treat conditions associated with natural estradiol deficiency.

WO 92/09266, Beecham Group, discloses a two-phase composition for topical drug application in which there are two liquid phases having different lipophilicities. Drug is dissolved in one of the phases such that a supersaturated state with respect to drug must result after mixing the liquid phases.

WO 92/17183, Glaxo, Inc., discloses a sequential dosing medicament and method therefor for topical treatment of fungal infections. The medicament comprises a first composition having an antifungal agent and an anti-inflammatory agent, and a second composition having only an antifungal agent as the active ingredient.

Accordingly, the present invention provides the transdermal delivery of a variety of types of drugs, which otherwise have low permeation rates and are generally incompatible with skin permeation enhancers during long-term combination, at therapeutically effective and significantly increased skin penetration rates, when used and applied as described herein. The present invention further provides the co-delivery and combining of drug having a low rate of skin permeation and a permeation enhancer which is unstable when mixed with the drug (or with vehicle for the drug) over a long period of time. In contrast to the art, the drug and permeation enhancer components of the invention are not permitted to interact prior to use, as a result of their physical separation in a suitable delivery device after preparation and during storage, before being topically applied and mixed on the skin at the site of application. Conveniently, the level or extent of penetration of the drug into the skin is advantageously and highly increased at the time of or shortly before use by mixing or blending the drug and permeation enhancer compositions directly on the skin to produce the desired active composition on the site of application by the user or applier.

SUMMARY OF THE INVENTION

The present invention provides methods and compositions to increase the bioavailability of pharmacologically active agents, or drugs, which are delivered into systemic circulation via a transdermal mode of administration following topical application. The invention is particularly advantageous for those drugs which have previously been administered by other methods, e.g., orally, intravenously, and the like, due to their low rate of penetration into the skin, or their inadequate efficacy following topical application, or their lack of stability in admixture with permeation enhancer compositions or formulations under normal storage conditions.

It is an object of the invention to provide an in situ active composition comprising drug and permeation enhancer for transdermal delivery, wherein, prior to formation of the active composition, the drug and the permeation enhancer are not compatible for long-term storage as a consequence of the instability of the drug in the presence of permeation enhancer and the formation of deleterious drug byproducts resulting from such instability. In accordance with the invention, the drug and permeation enhancer are separately housed and sequestered prior to use and application on the skin. Also in accordance with the invention, the drug and permeation enhancer are mixed or blended on the site of topical application at the time of simultaneously dispensing each of the component compositions onto the skin, thereby allowing the permeation enhancer to act on the drug at the time of use to significantly increase the rate of permeation of the drug into the skin. In accordance with the invention, the drug and permeation enhancer can also be premixed a short time prior to application on the skin, provided that the period of time that the component compositions are premixed results in minimal or virtually no degradation of the drug, thereby allowing a therapeutically effective amount of drug to be transdermally delivered.

It is another object of the invention to provide a method for increasing the skin permeation of a drug having an inherently low level of skin permeation by forming a composition comprising the drug and a pharmaceutically acceptable vehicle, carrier, or excipient, and forming another composition comprising a permeation enhancing agent with which the drug is generally not compatible for long-term storage, physically separating the compositions, and then co-dispensing and mixing the compositions to form a drug-active composition in which the skin permeation and absorption of the drug are greatly enhanced by the action of the permeation enhancer at the point of use.

It is yet another object of the invention to provide means for housing and delivering at least one drug-containing composition (the drug having a low rate of skin penetration) and at least one permeation enhancer composition. The invention provides a means to employ a drug and permeation enhancer which are incompatible, in that, when mixed, they interact with each other, or one or more of the drug and permeation enhancer interacts with the vehicle of the final composition, so that the long-term storage stability of such compositions is secured by keeping same physically apart. The sequestered compositions are then co-dispensed or co-applied to form the active composition in which both the drug and the permeation enhancer components are mixed together and the permeation enhancer increases the skin penetration of the drug at the time of topical application. As used herein, the active composition refers to the final composition as mixed on the skin. In addition, drug instability is reduced or alleviated because drug and permeation enhancer are not combined until just before or at the time of topical application on the skin surface. Drug degradation is also minimized or alleviated in accordance with the invention.

Yet another object of the invention is to provide a means to employ certain permeation enhancers for increasing the skin permeation of a drug even if these permeation enhancers and the drug cannot be mixed and stored together as a pharmaceutical composition because the permeation enhancer is incompatible with the drug over a long time period. Under conditions other than those of the present invention, the permeation enhancer is incompatible with the drug and/or the composition containing the drug over a long time period, thereby causing instability and degradation of the permeation enhancer. However, under the conditions afforded by the present invention, a pharmaceutically acceptable composition can be formulated comprising drug and permeation enhancer without the permeation enhancer becoming unstable over time and degrading to produce unwanted and/or potentially harmful byproducts.

Another object of the invention is to provide a means for performing a method for enhancing the skin penetration of any suitable topically-applied drug in the presence of a permeation enhancer, when the drug is unstable in the presence of such permeation enhancer during periods of extended storage. Thus, by the practice of the present invention, those in the art are able to combine any topically applied drug with any permeation enhancer, regardless of the incompatible nature of the drug and permeation enhancer during long-term storage, to enhance and augment the penetration of the drug through the skin of the user.

Another object of the invention is to provide a number of different formulations, which are separately housed or compartmentalized, to allow the improved skin permeation of a drug, which normally has a low rate of skin permeation, that is mixed with a permeation enhancer, even if the drug is unstable in the presence of permeation enhancer for long-term storage, or if the permeation enhancer is unstable in drug for long-term storage. In accordance with the invention, three separate formulations are provided: one of drug, a second of permeation enhancer, and a third of a vehicle. The three formulations are combined and mixed at the site of application at or shortly before the time of application on the skin. Also in accordance with the invention, two separate formulations are provided, particularly in the case in which a drug having a low rate of skin penetration and a permeation enhancer are compatible, but the two do not have long-term stability in the vehicle for the drug. One of the two formulations contains the drug plus permeation enhancer, and the second formulation contains the vehicle. The two formulations are mixed at the site of application on the skin at or shortly before the time of application.

Further objects and advantages afforded by the invention will be apparent from the detailed description hereinbelow.

BRIEF DESCRIPTION OF THE DRAWINGS

In describing the invention, reference will at times be made to the accompanying drawings in which:

(FIG. 5A) and at 40° C. (FIG. 5B) in a variety of excipient compositions as described in Example 2.

DETAILED DESCRIPTION OF THE INVENTION

Figure 1:
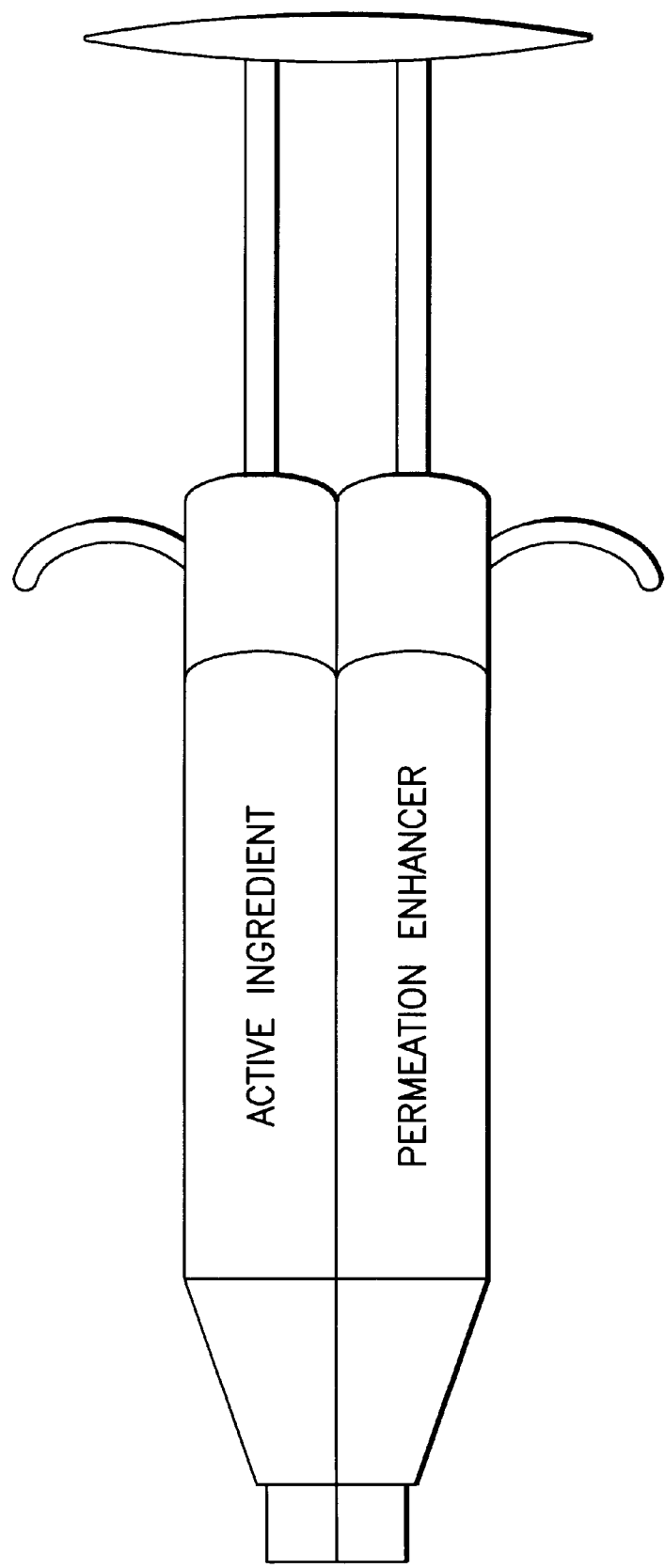
FIG. 1 depicts a schematic representation of a dual delivery dispensing assembly, e.g., a dual delivery syringe device, especially suitable for use in accordance with the dual delivery system of drug and permeation enhancer as described by the invention. As depicted, the dual delivery assembly is essentially a double barrelled syringe having two exit ports, one associated with each barrel. The two individual syringe chambers or syringe double barrels do not allow the contents stored therein to mix, blend or combine during storage. Further, a dispensing means (e.g., a plunger) serves to evacuate the contents of the syringe barrels through the two exit ports, such that the contents of the two barrels remain separate and apart until they are co-applied at a site on the skin, for example. In this device, a first exit port delivers the separately housed composition comprising the pharmacological agent (active ingredient), and the second exit port delivers the composition comprising permeation enhancer and/or solvent for the active ingredient, and the like, as described in the embodiments of the invention. It will be understood that, in accordance with one design, the dispensing means or plunger can work as single mechanism to control the evacuation of the two chambers at the same time by pushing the plunger toward the exit ports at the same time and at the same rate. Alternatively, in another design, a discrete plunger for each barrel can control the evacuation of the contents of each of the two barrels at different times and/or at varying rates. The dual delivery syringe device is capable of housing the active ingredient and permeation enhancer as separated compositions at room temperature, at 4° C., or frozen (e.g., –20° C.).

The present invention provides methods and compositions for enhancing the skin penetration or permeation of a topically applied drug or medicament, which, if applied alone, has a low rate of skin permeation or penetration, and which is unstable and/or incompatible with certain permeation enhancers conventionally known and used in the art. It is to be understood that the terms drug or medicament denote pharmacologically active compounds or agents (or topically active agents, compounds, or substances) which can confer a therapeutic and/or cosmetic benefit to the user. Such pharmacologically active compounds or agents also may include pharmaceutically acceptable salts or derivatives thereof. It is also to be understood that the terms pharmacologically active compound, drug and medicament are used interchangeably herein. In addition, the terms skin permeation and skin penetration are synonymous as used herein. The term skin retention denotes the amount of drug which permeates or penetrates the skin and is retained therein.

In addition, the invention allows enhanced skin permeation or penetration for transdermal delivery of a topically-applied drug or medicament which, if normally admixed and stored with particular skin permeation or penetration enhancers prior to use, demonstrates insufficient stability and degrades, thus forming unacceptable drug byproducts, which are potentially deleterious to the user. Moreover, the invention also allows enhanced skin permeation or penetration for transdermal delivery of a topically-applied drug or medicament which may cause instability and degradation of one or more particular skin permeation enhancers with which the drug is combined or mixed over a long period of time. Accordingly, the invention provides a means for employing virtually any drug with any permeation enhancer to enhance the skin permeation of the drug. The invention is appropriate and especially suitable for the topical application of a drug or drugs which are unstable in the presence of permeation enhancers during long-term storage, and thus, cannot be admixed or combined together for long periods of time prior to use.

It has previously been found that the dermal and transdermal penetration of a pharmacologically active compound could be substantially improved by incorporating the compound into a composition containing a dermal or transdermal penetration enhancing agent (also called a permeation enhancer), for example, as described in U.S. Pat. No. 5,326,566. However, a serious problem arises if the topically applied pharmacologically active compound has a low rate of skin permeation on its own and is incompatible with a given permeation enhancer, e.g., is chemically unstable, if incorporated into and stored in a composition or formulation comprising such a permeation enhancer.

The present invention affords a solution to this problem by providing a means for increasing and improving the skin penetration of a drug which, when ordinarily mixed with a skin permeation enhancer, is unstable and degrades, such that a stable mixture or combination of the drug and the permeation enhancer is neither attained nor sustained. The means for achieving the invention is carried out by physically separating the active component compositions, i.e., the drug in its pharmaceutical or dermatologically-acceptable vehicle or compatible solvent, from the permeation enhancer component composition until the time of use, when the two compositions are mixed or blended by the user or applier, to form the active composition comprising drug and permeation enhancer. The skin permeation of the drug in the latter composition is significantly increased relative to the rate of permeation of the drug in the absence of blending or mixing with the permeation enhancer. Drug and permeation enhancer can be mixed or blended either immediately before or at the time of topical application of the component compositions onto the skin surface. Preferably, the drug and permeation enhancer compositions are blended on the skin by the user. By vehicle is meant a pharmacologically acceptable, inert medium in which an active drug, medicament, or permeation enhancer is administered. Also encompassed by this term are the terms excipient, carrier and placebo, which may be used synonymously herein.

It is to be understood that the term permeation enhancer is intended to encompass any biological, chemical or pharmaceutical material, compound or agent which functions as a permeation enhancer to increase and/or enhance the penetration of a pharmacologically active compound into the skin. It is further understood that a permeation enhancer or any material serving as a permeation enhancer and/or having the function of a permeation enhancer in accordance with the invention is capable of increasing the rate of penetration of the pharmacologically active compound into the skin, particularly when the rate of the compound in the absence of the permeation enhancer, or the material which functions or serves as a permeation enhancer, is negligible to low.

Provided by the invention are one or more compositions comprising the drug of interest and a dermatologically-acceptable vehicle for the drug, such that the drug has long-term storage stability in the vehicle and exhibits a first rate of permeation when the drug-containing composition is applied to a body surface or skin area. As a general guide, long-term storage stability refers to the stability of drug when stored for at least about one year, preferably at least two years, and more preferably at least three years, and most preferably at least four years, when stored at room temperature. Also provided by the invention are one or more second compositions comprising a skin penetration or permeation enhancer for the drug, which, when ordinarily mixed with the drug, cause instability of the drug and drug degradation byproducts so that long-term storage stability of the drug in such a mixture is unattainable. The drug-containing composition and the permeation enhancer-containing composition are topically applied to an area of the skin, such that the application of the compositions is simultaneous or successive. If the application is successive, one of the compositions must be applied within a short time after the other composition is applied (e.g., within about one to thirty minutes of one another, preferably, within about five to ten minutes of one another, and more preferably, one directly or immediately after the other, e.g., within several seconds). The compositions are mixed, for example, by rubbing (e.g., using finger pressure) at the site of application, thereby forming a blended active composition in situ.

If the compositions are applied one after the other, the order of delivering or applying the compositions to the skin area is not expected to affect the performance of the invention; for example, when a first composition comprising drug and a second composition comprising permeation enhancer are employed, either the first or the second composition may be applied first to the skin. However, the order of application of drug and permeation enhancer may be important if the drug is in suspension in the first composition and dissolves in the solvent of the second composition containing the permeation enhancer. In such cases, it is preferred to first apply the drug-containing composition followed by the permeation enhancer-containing composition. Similarly, if the permeation enhancer is suspended and has to dissolve in the vehicle of the drug composition, then the permeation enhancer composition should be applied first. However, if both the drug and permeation enhancer compositions are in solution, either of the first or the second composition can be applied first.

In a preferred mode, one or more drug compositions is first applied to the skin followed by one or more permeation enhancer compositions, either immediately or shortly thereafter, i.e., within about ten minutes of one another, preferably within about five minutes of one another, more preferably one right after the other. Alternatively, the drug-containing composition and the permeation enhancer-containing composition may be mixed just prior to application, forming a premixture or blended composition, provided that the concentration of the drug is not thereby reduced below 90%, preferably not below 95%, and more preferably, not below 99% of the starting concentration. The premix should be typically applied with regard to the aforementioned concentration requirements. Usually, the premix will be employed within a day, preferably within a few hours, more preferably within about an hour, and most preferably, within minutes after forming the premix. Naturally, the time will vary with storage conditions and overall stability of the drug and permeation enhancer. Those skilled in the art will appreciate that refrigeration will extend the time that the premix can be employed. As a nonlimiting example, room temperature storage conditions may allow the premix to be employed within a day or several days, while refrigeration (e.g., 4–5° C.) may extend the time to a month, possibly to about two to three months.

As described above, when the application of the compositions is in the form of a premix, the time elapsed between the preparation of the premix and its topical application to a body surface or skin area is such that the concentration of the drug in the premix is not less than a predetermined acceptable concentration. For example, the drug concentration in the premix should not be less than 90% of the predetermined acceptable concentration, preferably not less than 95% of the predetermined acceptable concentration, and more preferably not less th 99% of the predetermined acceptable concentration. Upon mixture of the drug composition and the permeation enhancer composition on the skin to form a final active composition comprising drug mixed with permeation enhancer, as described hereinabove, a second rate of permeation of the drug is obtained, for example, a rate of at least about 2-fold to 5-fold, preferably at least about 10-fold, more preferably at least about 30-fold, and most preferably at least about 50 to 80-fold, or higher, than the first rate of drug permeation in the absence of the permeation enhancer. Moreover, by physically separating the drug-containing composition and the permeation enhancer-containing composition and then mixing the two compositions just at the time of application to produce the active composition on the body surface or skin, or by premixing the two compositions at an appropriate time prior to application on the skin and then applying the premix to the body surface or skin, the production and presence of one or more drug degradation byproducts in the active composition that is delivered to the body surface or skin area (and that could possibly permeate the skin due to the action of the permeation enhancer) are substantially reduced or alleviated.

As described herein, it is to be understood that more than one drug composition and/or permeation enhancer composition may be used in the invention, provided that all of the compositions are kept separated during storage and then are combined at the point of use.

In accordance with the invention, there is provided a method for topical treatment of the human or animal body, comprising applying thereto an effective amount of a pharmaceutical composition comprising drug and a separately-stored composition comprising permeation enhancing agent. The invention is particularly appropriate for a drug that is unstable in the presence of permeation enhancer under the conditions and timeframe of routine storage for pharmaceuticals. The invention further provides a method of obtaining, in a warm-blooded mammal, including humans, a desired degree of skin penetration of one or more of a pharmacologically active compound having, on its own, a low rate or level of skin permeation, and capable of having its skin permeation enhanced, but incapable of long-term compatibility or stability with one or more given permeation enhancers.

The proportion of the drug to the permeation enhancer in the active composition may be manipulated as practiced by those in the art by adjusting the concentrations of the components in any suitable manner, for example, by changing the size of the exit ports for each component. For example, FIG. 1 shows a double barrelled syringe device having regulatable cylinder and port sizes for dispensing the drug and permeation enhancer compositions in accordance with this aspect of the invention. In the device exemplified in FIG. 1, the diameters, as well as the size of the exit ports, of the two barrels of the syringe can be varied or changed independently to result in the delivery of the required amounts of the two compositions which are contained in each of the syringe barrels.

The present invention also encompasses the ability of the skilled practitioner to adjust the degree and amount of permeation into the skin after application of drug and permeation enhancer, for example, by varying the amount of enhancer to produce a predetermined amount for mixing with drug and having maximal thermodynamic activity for permeation. Accordingly, by varying or tailoring the amount or degree of permeation enhancer that is applied, the degree of skin permeation can vary. This aspect of the invention can be achieved by using different means of administration in which the amount of permeation enhancer is adjusted to attain a particular degree of permeation. As a nonlimiting example, the concentration of drug may be 1%, by weight, while the concentration of permeation enhancer may vary from 0.1 to 0.3%, for example, to achieve a variable flux and rate of permeation. As another example, using a dual syringe model, the administration of permeation enhancer may begin with a minimum rate of input and can build up to a greater depth of permeation in the skin by varying the input rate to a maximum rate. Alternatively, the input and output rates of permeation enhancer may be regulated, such that a device is designed to allow different permeation rates. In this way, a treatment may be initiated at one rate, and then the rate may be increased (or decreased) during the course of administration or at a later time of administration. Another alternative involves the use of two devices, such as dual syringe devices, in which one syringe is employed to afford a first degree of permeation and a second syringe is employed to afford a second degree of permeation at a later time of administration. Such a regimen may be followed to afford different degrees of permeation using a series of different syringes which are designed to deliver varying amounts of permeation enhancer after application on the skin.

The method in accordance with the invention can be practiced by employing various delivery systems in which the drug-containing compositions and the permeation enhancer-containing compositions may be physically separated, compartmentalized, housed, sequestered or stored prior to their actual mixture when applied topically to the skin. As a particular but nonlimiting example, if one drug-containing composition and one skin permeation enhancer-containing composition are employed, a dual-delivery system is advantageous for use.

In general, devices for housing and dispensing the pharmacologically active composition and the permeation enhancer composition of the invention, prior to application and blending of the compositions, may be in the form of collapsible or flexible tubes, rigid tubes, bottles, jars, ampoules, spray dispensers (e.g., aerosol cans), transdermal patches, impregnated pads, syringes, pumps, other dispensers, capsules, microcapsules, microparticles, or any other suitable or appropriate presentation known in the art. The dispenser used in the invention will optimally keep the pharmacologically active composition out of physical contact with the permeation enhancer composition during storage and until the time of use, or shortly beforehand.

One type of housing and dispensing device is unitary, i.e., comprises a single container which cannot be broken apart, e.g., a single tube or a molded pair of tubes or cylindrical shaped receptacles, whereby the same device and the same dispensing mechanism and aperture are used for application of both the drug-containing composition and the permeation enhancer-containing composition. A number of designs for devices suitable for use in the invention are available to those skilled in the art. For example, various dispensers and devices suitable for use, or which may be modified by the skilled practitioner to have the features necessary for separately compartmentalizing and subsequently co-applying or sequentially applying the compositions of the invention, may be found in the disclosures of U.S. Pat. Nos. 4,823,985; 5,156,846; 5,223,262; 4,592,487; 4,379,454; 4,497,794; WO 92/17183; and Spanish Patent P.8803996.

Other dispensing devices useful in the present invention are as described hereinbelow. For example, a single cylindrical jar or container provided with a vertical wall along the diameter line to define two compartments may be used to separate and contain a pharmacologically active composition having a first, low permeation rate (e.g., the first composition) and an incompatible permeation enhancer composition (e.g., the second composition) in which the pharmacologically active composition is unstable, in accordance with the invention. Also, two separate devices may be used, i.e., one device for each of the first and second compositions.

A single device may be used for housing and dispensing both compositions, wherein there is a sequential dispensing of the first composition followed immediately or a short time thereafter by the second composition from the same device. The sequential dispensing, i.e., the switching from the first to the second composition, may be manual or automatic. Alternatively, the single dispensing mechanism can be such that the separately housed first and second compositions within in the device are capable of being simultaneously delivered from the same aperture or port, or side-by-side apertures or ports, of the same device at the time of application.

In a manual operation, as but one example, the individual or physician would adjust the device, e.g., by a dial, to dispense the first composition and would then re-adjust the device to dispense the second composition. Alternatively, the device in the manual operation would be preset to dispense the first composition and would then be manually adjusted to dispense the second composition or vice versa. In an automatic operating device, as another example, the device would dispense the first composition which had been pre-filled to a preset amount and only upon its exhaustion would the device then dispense the second composition. In the automatic mode, the individual could be unaware that a different composition was being dispensed after the switch. Alternatively, the device may dispense a preset number of applications of the first composition, i.e., the low permeation rate, pharmacologically-active composition, rather than a preset amount of the first composition. The device would then automatically switch from the first to the second composition; at that point the user would be unable to dispense more and would know to use the second composition at that time. In such a mode, for example, the device would dispense about 7, 14, 28, or 56 times, depending upon whether the first compositions was to be dispensed for 7 or for 14 days and whether dosing was to be 4 times per day, 2 times per day, or 1 time per day. These parameters could be programmed into the device at manufacture or by the pharmacist depending upon the physician's prescription.

Figure 2:
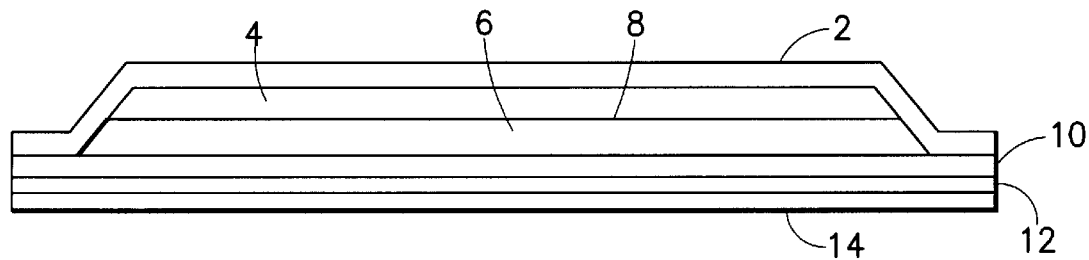
FIG. 2 depicts a schematic representation of a transdermal delivery device suitable for use in accordance with the invention. The component parts as shown in the device include a backing layer (2); a formulation containing drug (4); a formulation containing permeation enhancer (6); an impermeable membrane rupturable with pressure (8); a diffusion membrane (10); a contact adhesive layer (12); and a removable release liner (14).
Figure 3:
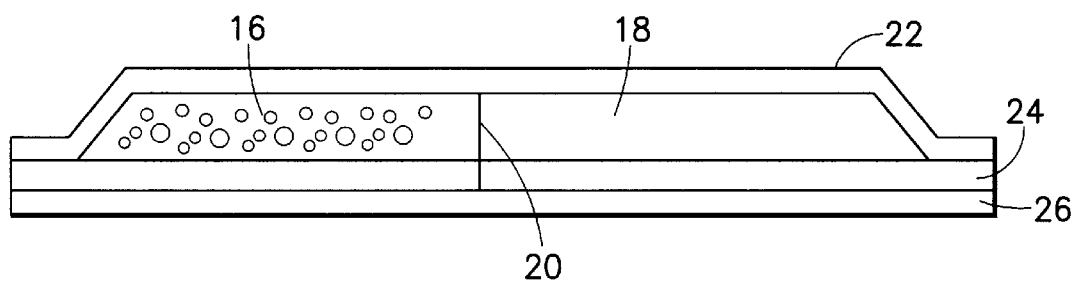
FIG. 3 depicts a schematic representation of another transdermal delivery device suitable for use in accordance with the invention. The components parts as shown include a formulation containing drug (16); a formulation containing permeation enhancer (18); an impermeable membrane which is broken apart by finger pressure (20); a backing layer (22); an adhesive layer (24); and a removable release liner (26).
Figure 4:
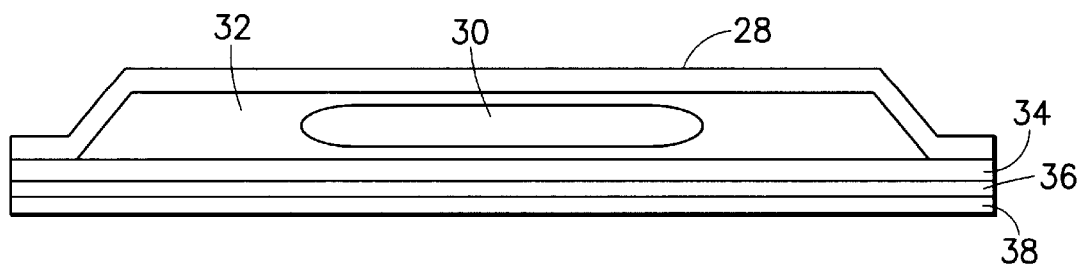
FIG. 4 depicts a schematic representation of yet another transdermal delivery device suitable for use in accordance with the invention. The components parts as shown include a backing layer (28); a formulation containing drug housed within an impermeable capsule broken upon pressure (30); a formulation containing permeation enhancer surrounding the impermeable capsule (32); a diffusion membrane (34); a contact adhesive layer (36); and a removable release liner (38).

For two compositions comprising the invention, wherein one composition comprises a drug in a pharmaceutically acceptable vehicle, carrier or excipient, and the other composition comprises a permeation enhancer, the compositions may be specifically packaged in a dual delivery device, a twin compartment pack, or transdermal delivery system ready for topical application by the user or patient (for example, see FIGS. 2, 3 and 4). The user or patient would normally apply the two compositions simultaneously on the treatment or skin area and then mix the compositions together in situ via finger pressure and a rubbing motion to create the active treatment composition for topical penetration. The two compositions can also be mixed in the pack or device by breaking a membrane or seal separating the first and second compositions, thereby creating a solution or emulsion in the pack for topical administration or application of the active composition onto the skin. Suitable packs and devices for such purposes are commercially available.

The methods and compositions embodied by the invention provide a means by which a number of different drugs or medicaments, which have poor topical absorption, or which are required at high dosage levels, can be effectively topically administered, e.g., in a transdermal system. Accordingly, a preferred means of housing and delivering a physically separated drug composition and permeation enhancer composition to the skin is that of the transdermal patch or a similar device as known and described in the art. Examples of such devices are disclosed in U.S. Pat. Nos.

5,146,846, 5,223,262, 4,379,454 and International application number WO 92/17183. The transdermal mode of storing and delivering the compositions onto the skin and forming the active composition is convenient and well suited for the purposes of the invention. In general, a transdermal device for delivering the compositions in accordance with the invention is comprised of two chambers, reservoirs, or compartments which are physically separated by an impermeable membrane, wall, seal, or divider which is collapsible and rupturable when purposefully ruptured by the user, immediately prior to or just at the time of topical attachment of the means or device onto the skin surface (see FIGS. 2–4). The membrane, and the like, provide separate and discrete storage of the two compositions and do not allow leaching or diffusion of the contents of one compartment into the other compartment during normal and routine manufacture, packaging, storage, and eventual application onto the skin prior to rupture of the membrane.

The underside of the lower or basal surface of the transdermal device is affixed to a selected localized area of the skin; the upper surface is essentially parallel to the skin surface and may be elevated or raised away from the skin surface. In one of the separated compartments of the device is housed the drug composition which is stable as formulated in a pharmacologically acceptable vehicle. In the second compartment is housed the composition comprising permeation enhancer. Following application of the transmembrane device to the skin, deliberate and sustained finger pressure on the upper surface of the device collapses and breaks the membrane or divider between the compartments and the two compositions, formerly maintained separately, are mixed together by a circular or vigorous rubbing motion by the fingers on the surface of the patch to produce on the skin the active composition comprising drug and also permeation enhancer.

If the device is designed to contain more than two separated compartments, other pharmaceutically acceptable compounds, including different types of drugs and/or permeation enhancing agents, may be stored therein, mixed and transdermally administered to an individual as desired or warranted. In this regard, an embodiment of the invention involves more than one drug composition and/or more than one permeation enhancing composition, which can be contained separately, in discrete compartments, containers, reservoirs, and the like, depending upon the nature of the storage and dispensing device, until topically applied on a skin site. Mixing or blending of the various compositions may then occur as described above, at the same time after application, or immediately or a short time following application of the compositions to the skin. In addition, a premixture of the component compositions of the invention, or a subset thereof, can be made immediately or a short time prior to topical application on the skin, and the other component compositions can be admixed and combined with the premixture at the time of topical application.

Thus, in view of the foregoing, it is to be generally understood that a variety of devices and containers for housing and/or storing and applying drug and permeation enhancer and their pharmaceutically acceptable carriers, excipients, or formulations may be used in the invention. The nature of the device should not impact on the scope or operability of the method, provided that the composition comprising drug and the composition comprising permeation enhancer are kept separated during storage, and are not allowed to mix or combine until the time of use, immediately before use, or a short time prior to use. The compositions may be premixed, either inside or outside of the device, a short time before use, and then the final active composition is topically applied to the skin.

Another novel storage and delivery means for sequestering the active drug component away from the incompatible permeation enhancer component prior to use involves dissolving or formulating the drug in a compatible pharmaceutically-acceptable solvent or excipient vehicle, and then encapsulating the drug solution or formulation in microcapsules, microparticles, microspheres, or combinations thereof, and the like. The drug-containing microcapsules, and the like, are suspended in a suitable composition, such as a gel or cream and the like, which contains a permeation enhancing agent and serves as an outer solvent in which the drug-containing microcapsules are suspended. In such a storage and delivery means, the microcapsules, for example, are made of a substance or material that does not permit diffusion into or out of the microcapsule and does not allow leaching out of its contents to any significant extent. However, the microcapsules are capable of being ruptured, broken, or split by using finger pressure, for example, after the composition containing the microcapsules is applied to the skin and rubbed or blended on the skin surface by the user. The rubbing or blending of the composition comprising drug-encapsulated microcapsules at the time of application onto the skin allows the drug to be released from the ruptured, broken or split microcapsules and permits the mixing of released drug with the outer solvent containing permeation enhancer. Accordingly, a mixture and combination of active drug and permeation enhancer in a base composition as desired are provided to the user at the site of application.

In another aspect of the invention, it is envisioned that a plurality of compartments, chambers, reservoirs, containers, bottles, or vials, and the like, depending on the device or delivery means used, can separately contain a number of components comprising the drug composition, and/or the permeation enhancer composition, i.e., multicomponent compositions. The separated components are ultimately mixed at or near the time of use to form the active composition. The mixing of the components can occur at the time of topical application and blending on the body or skin surface. Alternatively, the components may be premixed to form the drug composition and the permeation enhancer composition and the two compositions may be applied to the skin and mixed thereon within a defined period of time after the formation of the premixture, thereby forming the active composition. In this manner, for example, the components of a drug composition may be separated prior to use, and then mixed together to achieve the complete drug composition at the time of use. The complete drug composition is mixed with the composition comprising permeation enhancer, also at the time of use, to produce the active drug composition having enhanced skin penetration.

Drugs useful in the present invention may be in any pharmaceutically acceptable chemical form, such as acid, base, salt, ester, ether, amide, amine, and the like. The drug can be oil-soluble and/or water soluble or soluble in pharmaceutically acceptable solvents, such as alcohols, glycols, and ethers. As but one example of this innovative aspect of the invention, a component of a drug composition comprising a certain acceptable chemical form of the drug, for example, a salt or an acid, is housed in one compartment. A composition comprising a permeation enhancer in a formulation for topical application, e.g., gel, cream, ointment, lotion, solution, and the like, is housed in a second compartment. An appropriate excipient vehicle for the drug and permeation enhancer components is housed in a third compartment, the vehicle excipient having particular characteristics, such as pH, ionic strength, buffer capacity, solventability, and the like, which, when mixed with the contents of the first drug compartment and the contents of the second permeation enhancer compartment produces a thermodynamically active composition for the drug and permeation enhancer, such that they have maximum activity to partition and permeate across the skin. All three separately housed compositions are simultaneously or successively applied to the skin and blended or mixed by rubbing on the site of application to form the active composition thereon. The active composition comprises the effective and active chemical form of the drug, which is produced in situ after blending. Preferably, the relative amounts of the solvent, drug, and permeation enhancer present in the final active composition are such that the final composition is saturated with respect to the drug and the permeation enhancer. The pH, solvency, and ionic strength of the final active composition are designed so that maximum thermodynamic activity of the drug and permeation enhancer is secured, thus resulting in favorable partitioning of the drug into the skin. In the active composition, the composition comprising the salt or acid form of the drug and the composition comprising the permeation enhancer are mixed so as to enhance the penetration of the active drug into and through the skin by providing an increased penetration rate relative to that possessed by the drug in the absence of the permeation enhancer. This aspect of the invention encompasses the use of a drug in the form of a prodrug in one compartment, which is converted to the active form of the drug after mixing and blending with the appropriate excipient vehicle in a second compartment, as described above, and permeation enhancer on the site of application on the skin.

As a more particular example, the BMS-188184-01 di-acid phospholipase A2 inhibitor composition, as further described in Example 2 herein, may be prepared and placed in one compartment, a vehicle having a pH (e.g., a pH of about 7.9 to 8.5) may be prepared and placed in a second compartment, and a composition comprising dodecyl-N,N-dimethyl amino acetate, which is normally incompatible for long-term storage with the phospholipase A2 inhibitor compound in the first compartment and with the vehicle in the second compartment, may be prepared and placed in a third compartment. Following simultaneous application onto the skin, or premixing and then application of the premixture onto the skin a short time after forming the premixture, the three compositions are blended, and the solubilized form of the phospholipase A2 inhibitor is produced and combined with the preferred permeation enhancer, resulting in the active composition having a high rate of skin penetration. It is preferred that the final mixed active composition be designed such that it provides the maximum thermodynamic activity for the drug and permeation enhancer. It will be understood by those in the art that the number of compositions for preparation and use in the invention may be two or more, depending upon the nature of the drug and the formulations desired or needed to comprise the active composition comprising active drug and permeation enhancer. It is also to be understood that one or more drugs and one or more permeation enhancers may be prepared, separately housed, co-applied to the skin, or sequentially applied within a short period of time of each other, if necessary or desired. Of course, when multiple drug and permeation enhancer compositions are employed together, they must be compatible, safe and effective in the active composition that is formed for topical use and skin permeation.

Alternatively, a first composition comprising drug in a particular vehicle can be prepared and placed in one container and a second composition, which is the solvent for the drug and which also comprises the permeation enhancer, especially a permeation enhancer that causes instability and/or degradation of the drug, can be prepared and placed in a second container. When the first and second compositions are 1) co-applied onto the body or skin and mixed topically on the site; 2) sequentially applied within a short time of one another and mixed on the skin site, or 3) premixed and then applied to the skin a short time after premixing, the drug composition is solubilized in the permeation enhancing solvent composition and the skin penetration of thus-solubilized drug is enhanced over that of the drug in the absence of such solubilization.

It is to be understood that variations of the above-described aspects of the invention are envisioned and contemplated for use, with appropriate modification, if necessary or desired, for storage, delivery, and activity of compositions of drug and an incompatible permeation enhancer after topical application.

The compositions of the invention are suitable for any medical, cosmetic, protective, or other treatment of a body surface area in any part of the body, including the skin, scalp, nails, and oral, genital, and rectal mucosa, in the presence or absence of hair. As described hereinabove, the compositions encompassed by the invention are advantageous for delivering drugs to the systemic circulatory system via a transdermal route, in which a drug is applied topically for absorption through the skin for systemic therapy.

Examples of suitable pharmacologically or therapeutically active agents for topical application as used in the compositions and methods of the invention include, but are not limited to the following: anti-inflammatory agents, which reduce swelling, redness, burning, itching, or pain, such as steroids, including corticosteroids and glucocorticosteroids (e.g., hydrocortisone, prednisolone, betamethasone and triamcinolone); nonsteroidal anti-inflammatory compounds or NSAIDS (e.g., aspirin, ibuprofen, phenylbutazone and indomethacin); 5-lipoxygenase inhibitors (e.g., Ionapolene, DuP 654); lipoxygenase/cyclooxygenase inhibitors (e.g., benoxaprofen, tepoxilin, BI-L-93BS); phospholipase C inhibitors; phospholipase A2 inhibitors (e.g., manoalide, BMS-188184 as described herein, and related compounds described in U.S. Pat. No. 5,436,369, assigned to the assignee hereof); protein kinase C inhibitors (e.g., sphingosines); interleukin-1 inhibitors (e.g., IX-207-887); interleukin-1 receptor antagonists; 12-HETE inhibitors (e.g., DuP 630 and DuP 983); imidazoles and retinoids (e.g., trans retinoic acids (tretinoin), 13-cis retinoic acid (isotretinoin), retinyl esters (retinyl propionate); PAF antagonists (e.g., BN-50730 and PCA-4248); essential fatty acids and their analogues (e.g., CD554 and CD581); beta-2 agonists (e.g., salmeterol), beta-3 adrenergic receptor agonists (e.g., BMS-201620 and BMS-196085); anti-pruritics; anti-bacterials; anti-fungals, such as sulfonazole, nystatin, amphotericin B and griseofulvin; anti-yeast compounds; antibiotics, such as penicillins, cephalosporins, tetracyclines, polymyxin B, bacitracin, novobiocin, amoxicillin, streptomycin and erythromycin; antiseptics; anti-virals, such as acyclovir; anti-AIDS drugs, such as AZT, ddI, ddC and the like; anti-ichthyosis drugs, such as ammonium lactate; drugs to treat disturbed or abnormal keratinization of skin, i.e., drugs which normalize keratinization, such as α- or β-hydroxycarboxylic acid and related ketocarboxylic acids and esters, lactones or salt forms thereof; drugs to treat hyperpigmentation of skin, such as hydroquinone and 4-hydroxyanisole; anti-psoriasis compounds, such as anthralin, MC 903 and tretinoin; anti-acne compounds;

anti-dandruff compounds; anti-histamines, such as tripelennamine, triprolidine, diphenhydramine and chlorpheniramine; anti-plaque agents; local anesthetics; analgesics; beta-adrenoceptor blockers, β-blockers, such as propranolol, bupranolol, timolol and nadoxolol; bronchospasm relaxants; anti-cancer agents; antianginal agents and vasodilators, such as nitroglycerin, isosorbide dinitrate, dipyridamole and hydralazine; anti-hypertensives, such as clonidine, α-methyldopa, captopril, and spironolactone; anti-motion sickness agents, such as promethazine, dimenhydrinate and meclizine; sex hormones, such as estrogens, androgens, estradiol, testosterone, and progesterone; contraceptive agents; anti-asthma drugs, such as cromoglycic acid; antitussives, such as codeine, dextromethorphan and diphenhydramine; acetylcholine esterase (ACE) inhibitors, such as enalapril maleate; antiemetics, such as chlorpromazine and meclizine; anticoagulants; decongestants; analgesics, such as aspirin and ibuprofen; antipyretics, such as aspirin or acetaminophen; anti-baldness/alopecia treatment agents, such as minoxidil; antidermatitis compounds; anti-ulcer drugs, such as cimetidine and ranitidine; antispasmodics, such as dicyclomine hydrochloride and other drugs effecting the gastrointestinal tract, such as atropine; sympathomimetic amines, such as xylometazoline, phenylephrine and napthazoline; central nervous system active agents, such as amphetamine, phenylpropanolamine and butorphanol; diuretics, such as chlorothiazide, hydrochlorothiazide and benzthiazide; and compounds which have a beneficial effect on the skin, e.g., in the treatment of photoaging and UV-damaged skin, such as alpha-hydroxy acids, retinoids and arotinoids; vitamins and vitamin salts, or derivatives thereof, such as vitamin C, vitamin E, vitamin A; protein and peptide drugs, such as insulin, TGF-α and TGF-β.

It will be apparent to those in the art that, where appropriate, pharmaceutically or dermatologically acceptable salts of the above-described pharmacologically active agents may be used. By way of nonlimiting example, a pharmaceutically or dermatologically-acceptable salt embraces any pharmaceutically acceptable salt of a drug which has therapeutic properties in mammals, including humans. The preparation of such salts is well known to those skilled in the art of pharmaceuticals. In general, pharmaceutically acceptable salts of a drug may include acetates, maleates, napsylates, tosylates, succinates, palmitates, stearates, oleates, palmoates, laurates, valerates, sulfates, tartrates, citrates and halides, e.g., iodides, chlorides, hydrochlorides, bromides and hydrobromides.

Examples of dermatologically acceptable vehicles for formulation with a pharmaceutically active agent in the invention include, but are not limited to, any suitable nontoxic or pharmaceutically acceptable topical carrier material or vehicle, such as a solution, suspension, emulsion, lotion, ointment, emollient, salve, unguent, cream, gel, sol, cataplasm, plaster, patch, film, tape or dressing preparation, all of which are well-known to those skilled in the art of topical pharmaceutical formulation.

When a drug and/or permeation enhancer fails to give long-term storage stability in the active composition which is designed to yield maximum thermodynamic activity, modifications will have to be made depending upon whether the drug and/or permeation enhancer is oil soluble or water soluble. For example, if the drug is oil soluble, it can be suspended in an aqueous system or it can be solubilized or suspended in a nonaqueous oleaginous system to form a first composition having long-term stability. Similarly, if the permeation enhancer fails to provide long-term stability, it can be isolated away from the drug composition as a second composition. A third composition is then designed so that the drug and the permeation enhancer have maximum thermodynamic activity for drug and permeation enhancer when the final active composition is formed by mixing the three, separate above-described compositions.

The following hypothetical example should serve to clarify this aspect of the invention. In this example, a formulation must produce an active composition in which an oil-soluble drug and an oil-soluble permeation enhancer are present in amounts such that each has maximum thermodynamic activity; however, the drug and permeation enhancer, when combined, fail to provide the necessary long-term stability. One way that the present invention is able to resolve this problem is that the drug is suspended in an aqueous cream (oil-in-water emulsion) base as a first formulation, which is stored in a first compartment, then the permeation enhancer is dissolved in an oleaginous vehicle as a second formulation, which is stored in a second compartment. To insure solvency, a solvent, as well as pH modifiers and buffers, when necessary, are formulated as an aqueous gel base third formulation, which is stored in a third compartment. The contents of the first, second, and third compartments are mixed on an area of skin to be treated and are blended to produce the active composition at the point of use.

In general, the rate of skin permeation (i.e., the maximum thermodynamic activity) is in the order as follows: the skin permeation rate of an optimal solubilized solution (in other words, a saturated solution) is greater than that of a dilute solution. It is necessary to consider the effect of the combination of the solvents in the final active composition on the solubility of the drug whose permeation needs to be enhanced. For acids and bases, the rate of skin permeation is generally higher for unionized forms than for ionized forms. As stated above, it is preferred that the composition containing the permeation enhancer be designed to give the permeation enhancer its maximum thermodynamic activity in the final active composition. For example, permeation enhancers such as menthone and d-limonene perform optimally in alcoholic vehicles, while the skin permeation enhancer sodium lauryl sulfate performs optimally in aqueous compositions containing an optimum level of propylene glycol.

A wide variety of skin penetration or permeation enhancers exist which may be useful in the invention. As an optimal guide, a given permeation enhancer, or combination of enhancers, should provide at least 2-fold to 5-fold, preferably at least 10-fold, more preferably at least 30-fold, and most preferably at least 50 to 80-fold, or higher, enhancement of drug permeation into the skin, compared with the level of permeation in the absence of permeation enhancer. Examples of suitable skin permeation enhancers for use in the invention include, but are not limited to, alcohols (e.g., ethanol, propanol, nonanol); fatty alcohols (e.g., lauryl alcohol); fatty acids (e.g., valeric acid, caproic acid, capric acid); fatty acid esters (e.g., isopropyl myristate, isopropyl n-hexanoate); alkyl esters (e.g., ethyl acetate, butyl acetate); polyols (e.g., propylene glycol, propanedione, hexanetriol); sulfoxides (e.g., dimethylsulfoxide, decylmethylsulfoxide); amides (e.g., urea, dimethylacetamide, pyrrolidone derivatives); surfactants (e.g., sodium lauryl sulfate, cetyltrimethylammonium bromide, polaxamers, spans, tweens, bile salts, lecithin); terpenes (e.g., d-limonene, α-terpeneol, 1,8-cineole, menthone); alkanones (e.g., N-heptane, N-nonane); biodegradable skin permeation enhancers (e.g., dodecyl-N,N-dimethylamino acetate, N,N-dimethylamino isopropionate) and water. The permeation enhancers can be formulated as solutions, suspensions, emulsions, gels, creams, lotions, ointments, patches, dressings, liposomes, aerosol sprays, cataplasms, plasters, films, or tape preparations, all of which are well known to those skilled in the art of topical pharmaceutical formulations.

The selection of a particular permeation enhancer for use in the invention and the determination of the respective concentrations of drug and permeation enhancer can be optimized or changed as necessary or desired by the skilled practitioner by utilizing the skin permeation assays as described herein.

The compositions of the present invention may also contain other ingredients of the type commonly employed by those skilled in the art of formulating compositions for topical application. These may include, for example, carriers, emollients, surfactants, emulsifying agents, emulsion stabilizing agents, thickening agents, preservatives, anti-oxidants, polymers, chelating agents, fragrances, polymers, adhesives, synthetic membranes, and release liners.

Compared with cream formulations, petrolatum-based ointments generally provide superior skin permeation of pharmacologically active agents contained therein. This is due to the occlusive nature of such ointments. The invention allows the formulation of ointment compositions comprising pharmacological active(s) for mixing with cream compositions comprising permeation enhancer(s) having the appropriate proportions of components in the compositions to produce a cream active composition having an increased rate of skin penetration of the active(s) contained therein. Moreover, petrolatum-based ointments are greasy. In some instances, it may be desired to have less greasy and more cosmetically attractive topical products, such as creams, lotions, gels, and solutions, having skin penetrations of the pharmacological active that are similar to those of an ointment. The production and application of such desired products may be attained by the present invention.

As a general guide, a particular drug should not degrade significantly during its shelf life, especially when formulated with other components and/or with permeation enhancing agent(s); 90–95% of the drug should remain intact and active during its shelf life. For drugs having a poor stability profile (e.g., tretinoin solution USP), a 10 to 30% average is added to have at least a 1 to 4 year shelf life when stored at room temperature. A drug which degrades in a composition due to instability or incompatibility with other ingredients with which it is formulated may result in unacceptable levels of degradation byproducts over time. Such byproducts, if present in the composition when delivered or topically applied to the skin with a given permeation enhancer, or mixtures thereof, may enter the skin upon application and rubbing, thereby allowing unwanted breakdown products along with the undegraded drug to enter an individual's systemic circulation. As described, the methods and compositions of the invention provide significant advantages to the art by eliminating such drug degradation and the resulting potentially detrimental byproducts, thus allowing full permeation and activity of intact, active drug, in the virtual absence of drug byproducts. Similarly, the methods and compositions of the invention eliminate the instability and degradation of permeation enhancer which, when combined with certain drugs, may also may yield potentially hazardous byproducts during long-term storage with such incompatible drugs. In this regard, the invention further prevents the application of degradative byproducts (either from drug or permeation enhancer) to the skin, thereby alleviating the risk that such byproducts will inadvertently enter the skin and the systemic system of the user or recipient. The present invention also provides a method for avoiding the use of an overage for unstable drug with permeation enhancer. This results in significant cost savings, especially when the drug is very expensive.

Preferably, the pharmacologically active agent is present in the active composition from about 0.001% to 80%, by weight, more preferably, 0.01% to 20%, by weight, based on the total weight of the composition. However, the effective amount of a specific pharmacological agent will vary in accordance with parameters well understood by the physician or veterinarian. These parameters include the condition being treated, the age, gender, weight and physical condition of the individual, and the specific agent selected.

Moreover, in view of the foregoing description of the invention, it will be recognized that any particular and suitable combination of drug and permeation enhancer can be readily determined by those skilled in the art. It is also within the skill of those in the art to vary the respective concentrations of drug and permeation enhancer as necessary or required, so that the benefits and advantages of the invention will be recognized. As but one significant advantage of the invention is the ability to increase and/or enhance the permeation of a drug which does not penetrate the skin, or which only poorly penetrates the skin, by combining the drug, or a derivative thereof, with a permeation enhancer with which the drug is otherwise unstable and degrades. Accordingly, prior to the present invention, those in the art would have been disinclined to employ and combine a drug with a permeation enhancer, if the two were known to be incompatible and/or if degradation of one or the other was a consequence of their combination and use.

EXAMPLES

The examples as set forth herein are meant to exemplify the various aspects of carrying out the invention and are not intended to limit the invention in any way. Unless otherwise specified, it is to be understood that the concentrations of the component ingredients in the compositions of the invention are in %, w/w, based on the total weight of the composition.

Example 1

A. In Vitro Skin Penetration Study

The following test method may be employed with human skin to determine the epidermal, dermal, or transdermal penetration of pharmacologically active compounds used in the practice of this invention. The procedure is also applicable to skin of other warm-blooded animals, e.g., mice, rats, and rabbits.

1. Skin Preparation

Normal excised human skin obtained from surgical breast reduction, or human cadaver abdominal skin samples obtained from the Firefighters Skin Bank were used. The skin samples were stored in a freezer at −30° C. until needed. Only skin that appeared normal was used. Historical evidence of chronic illness, skin disease or skin injury excluded the use of such skin samples in the study.

The skin obtained from the Firefighters Skin Bank was supplied as sterile, split-thickness skin with most of the underlying dermis already removed. The skin was thawed and rinsed in normal saline for about 30 minutes prior to use.

The skin obtained from breast reduction surgery was full thickness skin. It was thawed at room temperature in normal saline, followed by freezing on a microtome with carbon dioxide and sectioning to a layer around 200 micrometers thick. It was then stored in normal saline at 5° C. until about 8 hours before use.

2. Skin Penetration

The skin sections were mounted on flat-top Franz diffusion cells with a diffusional cross-section of 0.636 cm$^2$ or 1.8 cm$^2$. A 50 or 100 microliter sample of a test formulation was placed on the stratum corneum surface of the skin in the donor compartment and the receptor compartment was filled with 4 to 8 ml of normal saline, buffered solution, pH 7.4, or 30% isopropanol in water. The selection of receptor fluid depended on the drug candidate whose penetration had to be evaluated. The main objective was to maintain sink conditions in the receptor compartment. The receptor fluid was well stirred throughout the experiment and the temperature was maintained by circulating water at 37° C. through the water jacket of the diffusion cell. A 150 to 500 microliter sample was withdrawn from the receptor compartment at appropriate intervals and analyzed for drug content by HPLC or by scintillation counting to detect radioactive drug (i.e., labelled with $^{14}$C or $^3$H). The receptor fluid was replenished after each withdrawal. All of the receptor fluid employed was thoroughly degassed before use.

3. Skin retention (preparation of epidermis and dermis for analysis)

After the 44 hour or 68 hour skin permeation study, the stratum corneum was washed three times with 0.5 ml of alcohol, and then one time with 0.5 ml of 3% Tween 80 aqueous solution, followed by three washes with 0.5 ml of deionized water. Cotton swabs (Q-tips) were used during the rinsing procedure to recover the remaining surface dose. A circular incision was made on the skin exposed to the formulation. The epidermis at the circular edge was slowly lifted using a pointed flat spatula, and then separated from the dermis using forceps, the epidermis and dermis were transferred to previously-weighed teflon tape and dried in a dessicator for 72 hours until a constant weight was obtained. When 30% isopropanol in water was used as a receptor fluid, the epidermis and dermis could not be separated; in this case, the entire skin exposed to the formulation was rinsed as described above and cut and transferred to previously-weighed teflon tape and dried for 72 hours. The dried skin having a known weight was then transferred to a 5 ml volumetric flask, 2 ml of Soluene-350 was added, and the flask was placed in a 30° C. oven for 24 hours or more until the skin sample had completely dissolved. The contents of the volumetric flasks were then QS'd to 5 ml with absolute ethyl alcohol, filtered and analyzed for drug content by HPLC. When radioactive $^{14}$C or $^3$H-labelled drugs were evaluated for skin retention, the skin dissolved in Soluene-350 was mixed with Hionic Fluor solution and stored at 5° C. for 12 hours before counting for radioactivity.

Example 2

(2Z,4Z)-3-methyl-4-(3-carboxyphenyl)-5-[(1,2,3,4-tetrahydro-1,1,4,4-tetramethyl)-6-anthracenyl]-2,4-pentadienoic acid (BMS-188184) is an effective phospholipase A2 (PLA2) inhibitor synthesized by Bristol-Myers Squibb Company, as described and taught in U.S. Pat. No. 5,436,369, the disclosure of which is incorporated herein by reference. The drug compound is useful as a di-acid ($C_{31}H_{32}O_4$; MW 468.6; Bristol-Myers Squibb designation: BMS-188184-01) and as a di-potassium salt ($C_{31}H_{30}O_4K_2$; MW 544.78; Bristol-Myers Squibb designation: BMS-188184-02). While the di-potassium salt is soluble in water-based formulations, the di-acid was found to be virtually insoluble in water or oil-based formulations. The di-potassium salt form of the PLA2 inhibitor drug BMS-188184-02 was routinely used in the experiments as described herein. In addition, the phospholipase A2 inhibitor drug, BMS-188184-02, as described in the Examples herein, was found to be unstable in, and incompatible for long-term storage with, a number of permeation enhancers, such as surfactants, fatty acids, polyols, and various pharmaceutical solvents, e.g., water, polyethylene glycol (PEG), alcohol, and propylene glycol and Transcutol™ (ethoxydiglycol).

Figure 5A:
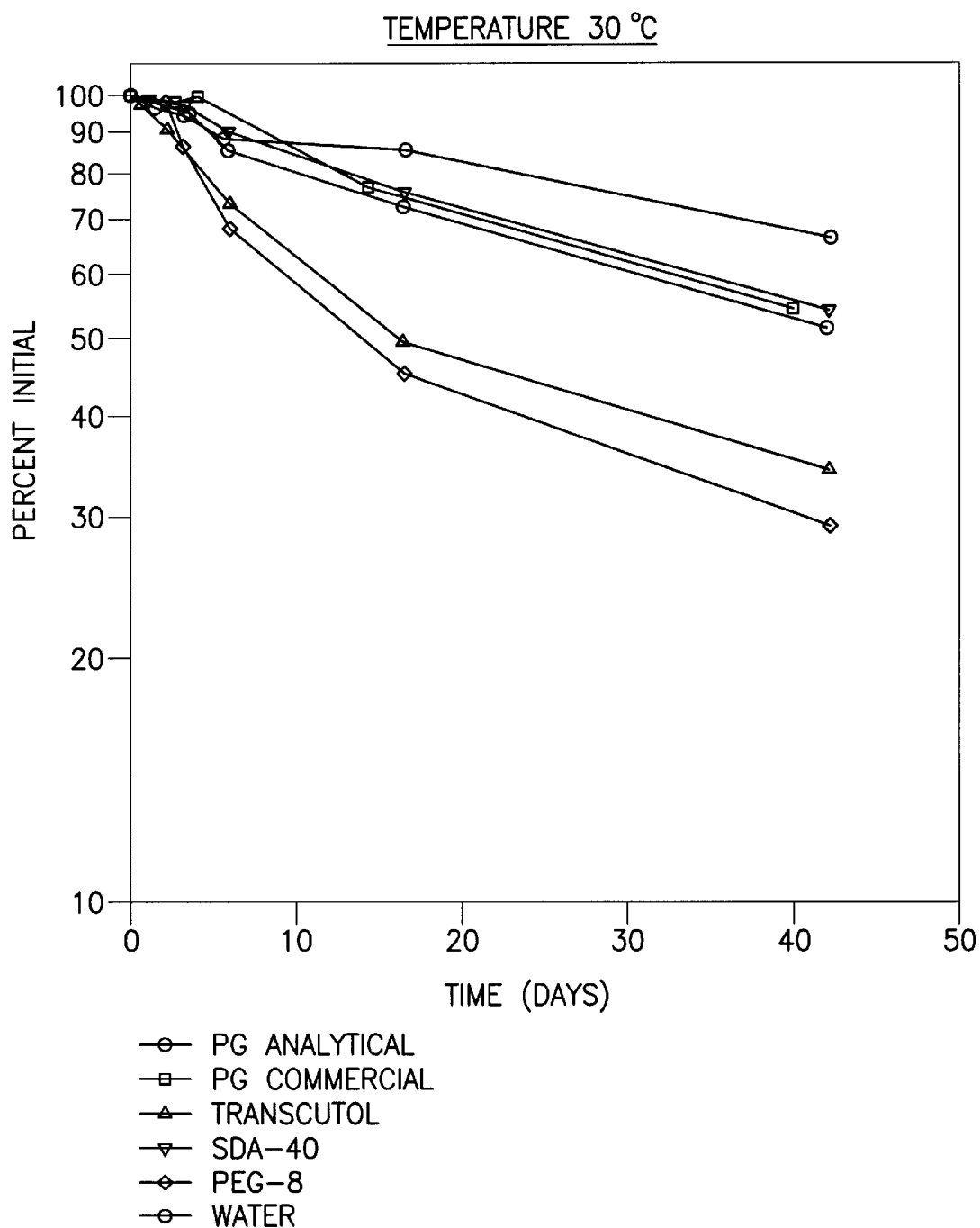
FIGS. 5A and 5B show the results of excipient stability studies to determine the long-term stability of BMS-188184-05 at 30° C.
Figure 5B:
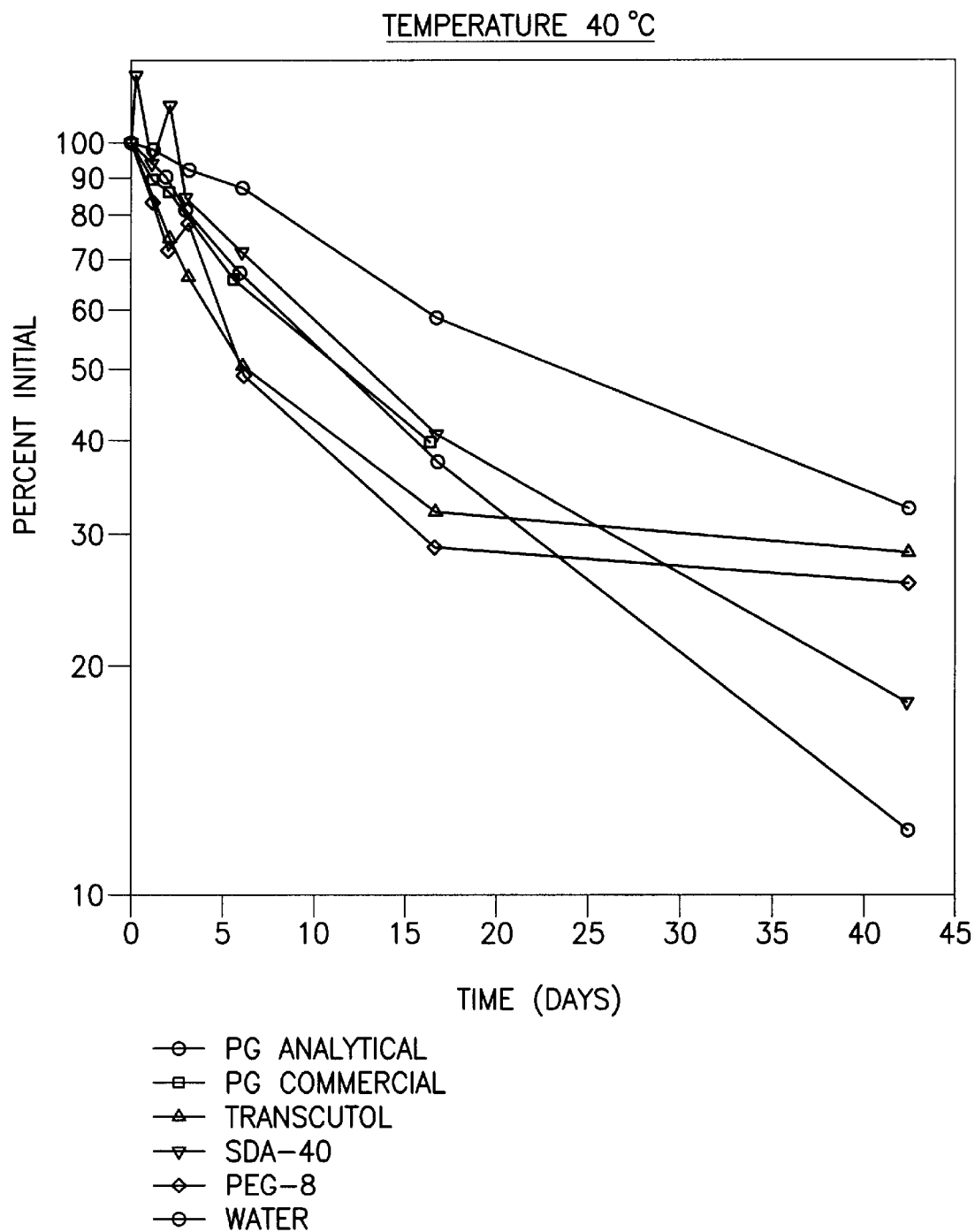

BMS-188184-01 and its salts are very unstable in the presence of light, surfactant, emulsifying agents, heavy metal impurities, peroxides and various pharmaceutical solvents. In addition, the stability of BMS-1881844-05 (di-n-methylglucamine salt) was evaluated (FIGS. 5A and 5B) in various pharmaceutical solvents, i.e., propylene glycol (PG) commercial grade, propylene glycol analytical grade, Transcutol™, ethanol SD-40, PEG-8, and water at 30° C. and 40° C. over time. The results indicate that the stability of BMS-188184 in these solvents is poor. As less than 90% of the drug was present with respect to its initial concentration within 10 days, the shelf life of BMS-188184 in these solvents at 30° C. will be less than 10 days. This example clearly illustrates the lack of long-term storage stability of BMS-188184 (particularly if combined as a single phase composition) in the presence of skin permeation enhancers such as propylene glycol, PEG-8, ethanol SD40, water, and ethoxydiglycol.

Example 3

In vitro human skin permeation studies were conducted using 1% BMS-188184-02 formulations described in Tables 1 and 2 which follow.

TABLE 1

GEAHLENE∓∓ Base Experimental Formulation of 1% BMS 188184-02

| Ingredients | Formulation 1 % w/w | Formulation 2 % w/w |
|---|---|---|
| BMS-188184-02* | 1.26 | 1.26 |
| GEAHLENE 16000** | 66.74 | 61.74 |
| Mineral oil | 20.00 | 20.00 |
| Aluminum Starch octenylsuccinate | 6.00 | 6.00 |
| Stearyl alcohol | 4.00 | 4.00 |
| Cetyl alcohol | 2.00 | 2.00 |
| BMS-203322 | — | 5.00 |

*BMS-188184-02 content is equivalent to 1% di-acid BMS-188184-01.
**GEAHLENE 16000 is a proprietary composition comprising mineral oil (and) hydrogenated butylene/ethylene/styrene copolymer (and) hydrogenated ethylene/propylene/styrene copolymer.

TABLE 2

Ointment Formulations of 1% BMS-188184-02

| Ingredients | Formulation 3 % w/w | Formulation 4 % w/w | Formulation 5 % w/w |
|---|---|---|---|
| BMS-188184-02* | 1.266 | 1.266 | 1.266 |
| Dibutyl adipate (DBA) | 20.00 | — | — |
| Ozokerite | 8.00 | 7.00 | 7.00 |
| Pterolatum | 49.584 | 66.584 | 66.584 |
| BHT** | 0.100 | 0.100 | 0.1 |
| Aluminum starch octenylsuccinate | 3.00 | 3.00 | 3.00 |
| Beeswax | 8.00 | 7.00 | 7.00 |
| Isopropyl myristate (IPM) | 10.00 | 10.00 | 10.00 |
| Ascorbyl | 0.05 | 0.05 | 0.05 |

TABLE 2-continued

Ointment Formulations of 1% BMS-188184-02

| Ingredients | Formulation 3 % w/w | Formulation 4 % w/w | Formulation 5 % w/w |
|---|---|---|---|
| palmitate | | | |
| Glycerol monocaprylate (GMC) | — | 5.0 | — |
| BMS-203322 | — | — | 5.00 |

*BMS-188184-02 is equivalent to 1% di-acid BMS-188184-01.
**Butylated hydroxytoluene Formulation 1 (Table 1) is a mineral oil vehicle thickened with proprietary polymer GEAHLENE and is henceforth referred to herein as GEAHLENE base. Formulation 2 (Table 1) is a GEAHLENE base formulation containing the known skin permeation enhancer, BMS-203322 (2 N-nonyl, 1,3 dioxane). Table 2 describes formulations in petrolatum ointment base with different known skin permeation enhancers. Formulation 3 (Table 2) contains dibutyl adipate (DBA) and isopropyl myristate (IPM) as skin permeation enhancers, while Formulations 4 and 5 (Table 2) contain IPM plus glycerol monocaprylate (GMC) or IPM plus BMS-203322, respectively, as skin permeation enhancers. It will be understood that in the formulations presented in Tables 1 and 2, the various ingredients have been employed due to their properties and/or functions in the formulations. Accordingly, other ingredients having equivalent or similar properties and/or functions may be substituted for a particular ingredient, if necessary or desired. Also, a particular ingredient is capable of performing more than one function. For example, in these formulations, DBA and IPM can function as emollients/permeation enhancers; petrolatum can serve as an occlusive/emollient; and aluminum starch octenylsuccinate can reduce greasiness and have emollient properties, as will be appreciated by those in the art. In addition, ozokerite and beeswax serve as thickening agents in Formulations 3, 4 and 5, while BHT and ascorbyl palmitate serve as antioxidants.

Figure 6:
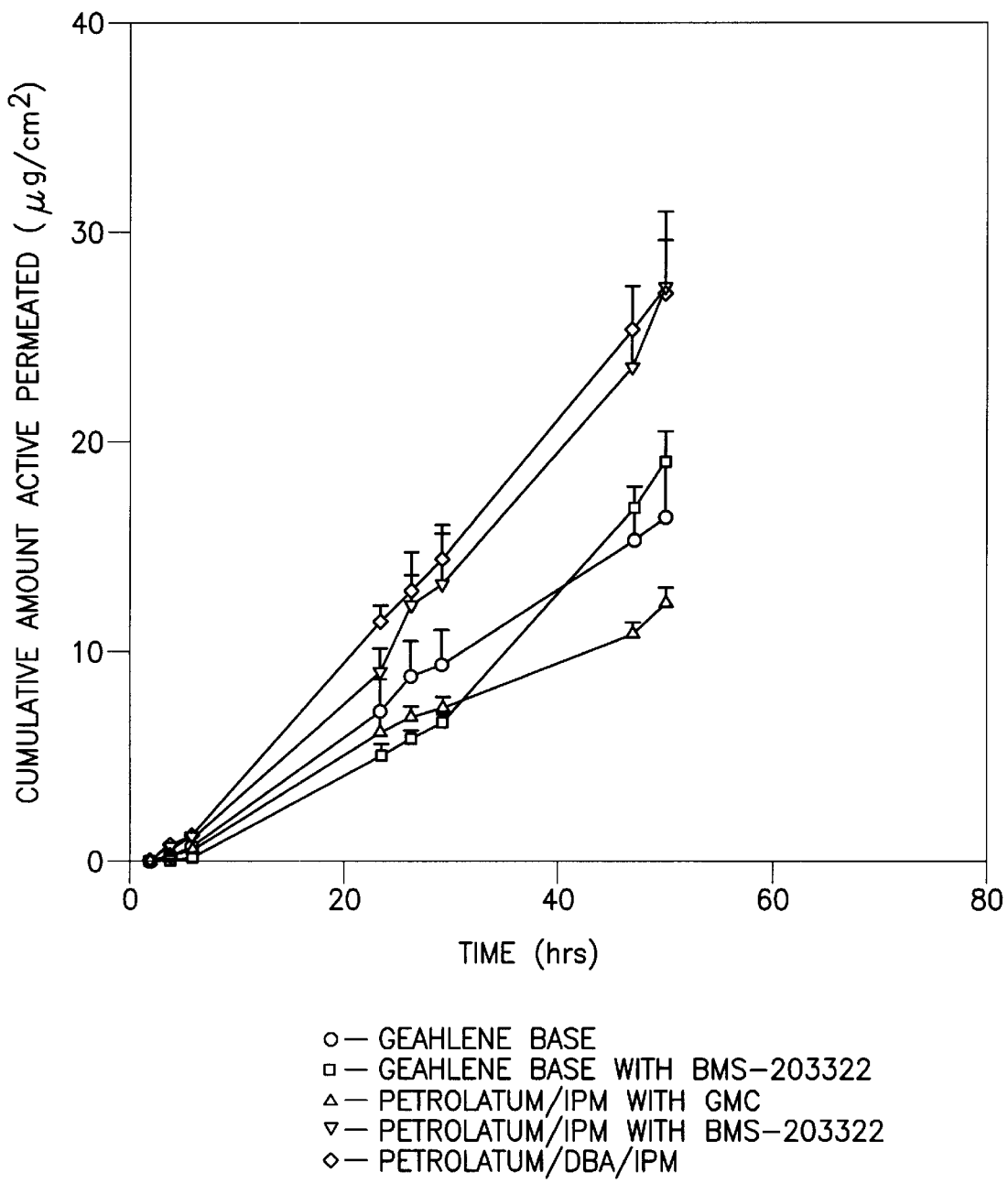
FIG. 6 and FIG. 7 present the results of in vitro skin permeation assays using the human cadaver skin model system. The assays determined the amount of penetration of phospholipase A2 inhibitor drug BMS-188184-02 from an active treatment composition comprising approximately 1%, w/w, of drug. (-●-: BMS-188184-02 1% in mineral oil base GEAHLENE ointment, as control); (-■-: BMS-188184-02 1% in mineral oil base GEAHLENE ointment with BMS-203322 skin permeation enhancer); (-▲-: BMS-188184-02 1% in petrolatum ointment composition with isopropylmyristate (IPM) and glycerylmonocaprylate (GMC) as skin permeation enhancer); (-▼-: BMS-188184-02 1% petrolatum composition with isopropylmyristate (IPM) and BMS-203322 as skin permeation enhancer); and (-♦-: BMS-188184-02 1% petrolatum ointment composition with dibutyl adipate (DBA)/isopropylmyristate (IPM) as skin permeation enhancer).
Figure 7:
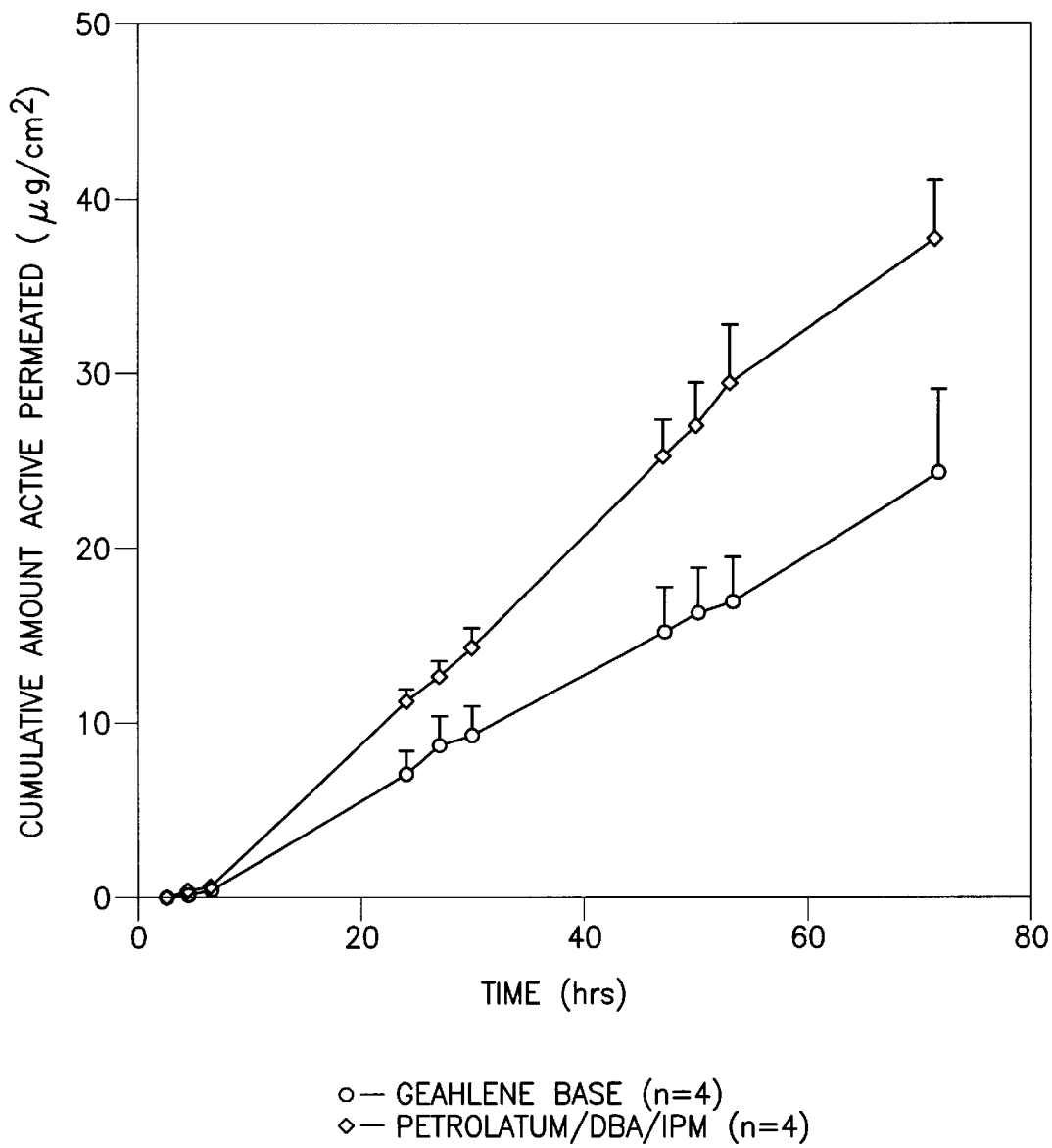

FIGS. 6 and 7 show the skin permeation profile of 1% BMS-188184-02 formulations described in Tables 1 and 2. The order of skin permeation was petrolatum ointment containing DBA/IPM (Formulation 3)=petrolatum ointment with IPM plus BMS-203322 (Formulation 4)>GEAHLENE base with BMS-203322 (Formulation 2)=GEAHLENE base (Formulation 1)>petrolatum ointment with IPM plus GMC (Formulation 5). Compared with GEAHLENE base (Formulation 1), ointment Formulations 3 and 4 (containing DBA/IPM and BMS-203322, respectively) demonstrated skin permeation enhancements of BMS-188184-02 on the order of 1.5-fold. This 1.5-fold permeation enhancement may not be significant enough to observe a difference in clinical activity. Accordingly, a minimum of 2-fold enhancement of skin permeation of drug is considered significant. The ointment formulation containing the known skin permeation enhancer GMC showed 50% reduction in skin permeation of BMS-188184-02 when compared with the GEAHLENE base formulation.

Thus, the results presented in this example suggest that one cannot a priori predict whether a skin permeation enhancer will increase the permeation of any particular drug; however, the present invention provides a means to increase the permeation of a particular drug, despite a low rate of permeation of the drug and an long-term incompatibility between a drug and a permeation enhancer. For example, in the present case, GMC may not have enhanced the permeation of BMS-188184-02 because it may have formed a complex with the drug, or the thermodynamic activity of GMC in the above-described nonaqueous petrolatum base may not have been sufficiently high. Therefore, it is important that the maximum thermodynamic activity of the permeation enhancer be in the final active composition. It is preferred to have GMC in an aqueous cream base formulation; however, since GMC is a surfactant in a water base, it is not compatible with BMS-188184-02 for long-term storage stability in aqueous formulations.

The accelerated stability of BMS-188184-02 in different formulations with permeation enhancers is shown in Table 3.

TABLE 3

Stability of 1% BMS-188184-02 In Formulations With Different Skin Permeation Enhancers

| Formulation/Permeation Enhancer | Drug Concentration Indicated As % Of Initial (4 weeks at 40° C.) |
|---|---|
| Ointment/Glycerol monocaprylate | 75% |
| Ointment/Caprilic acid | 82% |
| Ointment/Salicylic acid | 87% |
| Ointment/DBA and IPM | 100% |
| GEAHLENE base/None | 100% |

It is evident that BMS-188184-02 will not have long-term stability in the presence of skin permeation enhancers such as salicylic acid, caprilic acid and GMC in a single composition system. BMS-188184 is stable in GEAHLENE base containing mineral oil and in petrolatum ointment containing fatty acid esters, such as IPM and DBA. However, these permeation enhancers when used in a single composition/compartment system fail to show a two-fold or greater permeation enhancement of BMS-188184-02, compared with the GEAHLENE base formulation. Accordingly, the present invention provides a novel and advantageous means to overcome the limitations of using skin permeation enhancers with a drug in a single composition system, especially when the enhancers are incompatible with drug, or the drug is incompatible with the enhancers, and/or other ingredients or components in the final active composition.

Example 4

In vitro skin permeation experiments using human cadaver skin were conducted in which phospholipase A2 inhibitor drug was formulated into a first composition comprising the drug and pharmacologically acceptable ingredients to produce an ointment. The first ointment composition, which comprised the 2% di-potassium salt of the phospholipase A2 inhibitor drug, termed BMS-188184-02, formulated in petrolatum ointment is shown in Table 4, Formulation 6.

TABLE 4

Ointment Formulation of 2% BMS-188184-02

| Ingredients | Formulation 6 % w/w |
|---|---|
| BMS-188184-02* | 2.60 |
| Dibutyl adipate | 20.00 |
| Ozokerite | 8.00 |
| Petrolatum | 48.25 |
| BHT** | 0.10 |

TABLE 4-continued

Ointment Formulation of 2% BMS-188184-02

| Ingredients | Formulation 6 % w/w |
|---|---|
| Aluminum starch Octenylsuccinate | 3.00 |
| Beeswax | 8.00 |
| Isopropyl myristate | 10.00 |
| Ascorbyl palmitate | 0.05 |

*BMS-188184-02 is equivalent to 2% di-acid BMS-188184.
**BHT: Butylated hydroxytoluene The stability of a 5.0% ointment comprising BMS-1881844-02 in an ointment vehicle similar to that set forth in Formulation 6, Table 4, is shown in Table 5:

TABLE 5

| Time (Weeks) | Temperature (° C.) | Percent of Initial |
|---|---|---|
| 29 | 40 | 95.9 |
| 39 | Room Temperature | 97.3 |

A second composition comprising different permeation enhancers, which were incompatible if mixed and stored long-term with the phospholipase A2 inhibitor, was formulated as a cream to include petrolatum, dimethicone, steareth-2, steareth-21, laureth-23, cetyl alcohol, carbomer 934, sodium hydroxide, benzyl alcohol, diazolidinyl urea, propylene glycol, water, and either 2% decylmethylsulfoxide (Formulation 8, Table 6) as permeation enhancer or 0.8% sodium lauryl sulfate (Formulation 7, Table 6) as permeation enhancer.

TABLE 6

Cream Formulation Containing Skin Permeation Enhancers 0.8% SLS Or 2% Decylmethylsulfoxide

| Ingredient | Formulation 7 % w/w | Formulation 8 % w/w |
|---|---|---|
| Petrolatum | 15.0 | 15.0 |
| Dimethicone 200 | 2.0 | 2.0 |
| Steareth-2 | 2.5 | 2.5 |
| Laureth-23 | 0.5 | 0.5 |
| Cetyl alcohol | 2.0 | 2.0 |
| Carbomer 934 | 0.4 | 0.4 |
| Sodium hydroxide | 0.365 | 0.365 |
| Sodium lauryl sulfate | 0.80 | — |
| Water | | |
| Benzyl alcohol | 1.0 | 1.0 |
| Diazolidinyl area | 0.15 | 0.15 |
| Propylene glycol | 2.00 | 2.00 |
| Decylmethyl sulfoxide | — | 2.0 |

Another composition comprising a terpene permeation enhancer was formulated as a gel comprising SDA-40 alcohol (i.e., ethyl alcohol), hydroxypropyl cellulose, water, and either 5% menthone (Formulation 10, Table 7) as the terpene permeation enhancer or 5% d-limonene (Formulation 9, Table 7) as permeation enhancer.

TABLE 7

Gel Formulations Containing 5% d-Limonene or 5% Menthone As Skin Permeation Enhancer

| Ingredients | Formulation 9 % w/w | Formulation 10 % w/w |
|---|---|---|
| SDA-40 alcohol | 50.00 | 50.00 |
| d-Limonene | 5.00 | — |
| Menthone | — | 5.0 |
| Hydroxypropyl cellulose | 2.00 | 2.00 |
| Water | 43.00 | 43.00 |

The representative dual system formulations exemplified in Tables 4, 6 and 7 were designed to have maximum thermodynamic activity of drug and permeation enhancer when they were mixed together to form the final active composition. The first composition shown in Table 4 (Formulation 6) containing 2% BMS-188184-02 has long-term storage stability of the drug. The second cream compositions (Formulations 7 and 8) shown in Table 6 contained the skin permeation enhancers SLS (Formulation 7) and decylmethylsulfoxide (Formulation 8). These permeation enhancers have maximum thermodynamic activity in aqueous base cream containing an optimized amount of solvent and permeation enhancer (e.g., propylene glycol) and the occlusive agent petrolatum. The pH of the cream is about 7.5 to 8.3, which is an optimal pH environment for dissolving the drug BMS-188184-02. The cream was formulated to contain 2%, w/w, propylene glycol, which is just enough to form a saturated solution of the drug in the final active composition formed by mixing the drug and permeation enhancer compositions on the skin after the evaporation of water. Thus, the ointment/cream dual system is formulated so that the final active composition effectively and optimally permeates the skin.

The dual system of BMS-188184-02 ointment (Formulation 6, Table 4) with gel (Formulations 9 and 10, Table 7) containing terpenes, either 5% d-limonene or 5% menthone were designed as described above. The terpenes have maximum permeation enhancing activity in alcoholic base, hence, they were formulated in hydro-alcoholic gel formulations. The concentration of permeation enhancer depends not only on the type of permeation enhancer, but also on the drug whose skin penetration is to be enhanced. For example, a preferred concentration of SLS is about 0.005% to 1%, more preferably about 0.05% to 0.4%. For decylmethylsulfoxide, a preferred concentration is about 0.05% to 50%, more preferably 0.1 to 2.0%. For the terpenes menthone and d-limonene, a preferred concentration is 0.20 to 10%, more preferably 0.25 to 5%. The concentration of permeation enhancer that is required to enhance the permeation of drug into the skin can be determined by one skilled in the art by conducting routine in vitro human skin permeation experiments as described herein.

Figure 8:
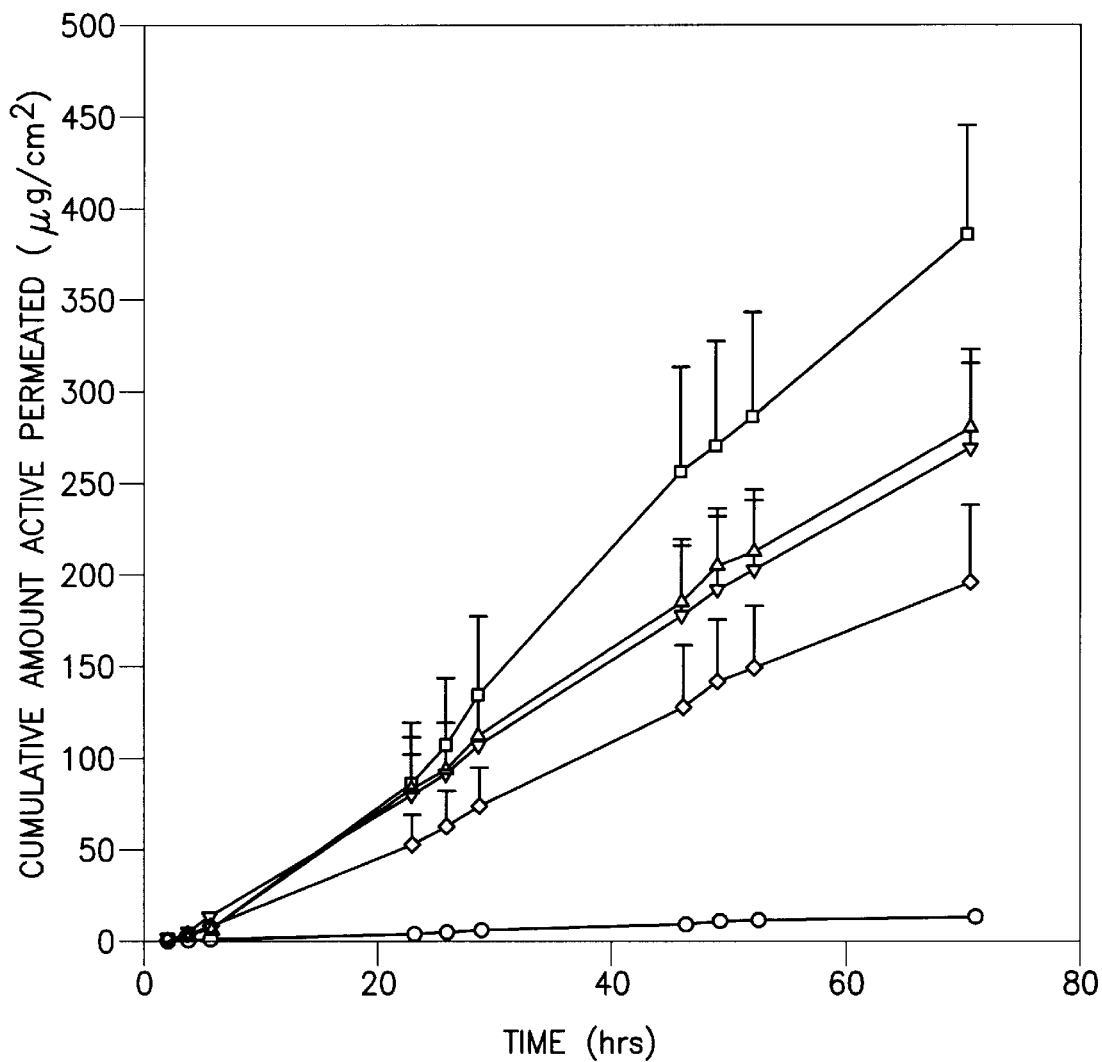
FIG. 8 depicts the results of in vitro skin penetration assays using the human cadaver skin model system. The assays determined the amount of penetration of phospholipase A2 inhibitor drug BMS-188184-02 from an active treatment composition comprising approximately 1%, w/w, of drug. In the dual system of the present invention, the active treatment composition of 1% BMS-188184-02 was formed by mixing the ointment-based drug composition with various cream- or gel-based permeation enhancer compositions and then immediately applying to the skin. (-●-: drug in mineral oil base ointment, GEAHLENE control); (-■-: active composition comprising BMS-188184-02 ointment composition, propylene glycol and SLS permeation enhancer cream composition); (-▲-: active composition comprising BMS-188184-02 ointment composition, propylene glycol and decylmethylsulfoxide permeation enhancer cream composition); (-▼-: active composition comprising BMS-188184-02 ointment composition and d-limonene permeation enhancer gel composition); (-♦-: active composition comprising BMS-188184-02 ointment composition and menthone permeation enhancer gel composition).

The human cadaver skin permeation studies were performed essentially as described in Example 1. The results of the skin permeation studies using dual delivery of a first drug composition and a second permeation enhancer composition are shown in FIG. 8. In the studies presented in FIG. 8, BMS-188184-02 was present in the final active composition comprising drug and permeation enhancer in an amount approximately equivalent to BMS-188184-01, 1.0% (w/w). Skin samples from four human subjects were used, and two replicates from each sample were analyzed for the cumulative amount of active drug permeated ($\mu g/cm^2$) over time (hours). As seen in FIG. 8, relative to the GEAHLENE mineral oil control (filled circles), the highest level of active drug that showed significant skin permeation was demonstrated using the ointment drug composition prepared as a first composition and delivered to the skin at the same time as the cream composition containing sodium lauryl sulfate (SLS) and propylene glycol as permeation enhancers, prepared as a second composition (filled squares). The first and second compositions were prepared and stored as separate compositions and were mixed and then applied to the skin surface.

A high level of skin permeation was also demonstrated for the active composition delivered and produced from a first ointment composition comprising drug and a second cream composition comprising propylene glycol and decylmethylsulfoxide (DeMSO) as an incompatible permeation enhancer composition (filled upright triangles). The active composition was obtained upon mixing of the first and second compositions and then applying on the skin site prior to performing and quantifying the permeation assay. A level of skin permeation of drug similar to that shown by the filled upright triangles, was observed for the active composition delivered and resulting from a first ointment composition comprising drug and a second gel composition comprising d-limonene, an incompatible permeation enhancer (filled upside-down triangles). An increased level of skin permeation, although less than those described above, was observed for the active composition delivered and resulting from a first ointment composition comprising drug and a second gel composition comprising menthone as the incompatible permeation enhancer (filled diamonds).

Example 5

In this example, in vivo skin permeation analyses were performed to evaluate the PLA2 drug BMS-188184-02 and the permeation enhancing agent SLS in a dual delivery system in accordance with the invention. In the dual delivery system as encompassed by the invention, a first composition comprising drug was prepared and a second composition comprising permeation enhancer was prepared. The drug composition was formulated as an ointment as described herein (Formulation 6, Table 4), and the permeation enhancer composition was formulated as a cream as described (Formulation 7, Table 6). The first and second compositions were prepared and stored separately and were delivered to the skin at the same time and were mixed together on the skin surface in a 1:1 proportion, by volume, to form a final composition comprising active drug and permeation enhancer, which is the active composition.

Skin concentrations of the drug were determined in the viable epidermis and dermis layers of the skin after topical application. The hairless rat system was the experimental model system used for these analyses.

Briefly, a 25 µl aliquot of the test formulation was applied on the dorsal skin of hairless rats on a surface area of 5 cm$^2$. At various times after application, the animals were sacrificed and the treated area of the skin was excised. The stratum corneum was removed by a cyanoacrylate stripping method. This method removes 98.5% of the stratum corneum and therefore eliminates any residual surface drug contamination. The stripping method is performed as follows: A thin layer of cyanoacrylate was applied to a standard sized glass microscope slide and was placed directly on the excised skin. The glue was allowed to dry for 5 minutes prior to stripping the skin from the slide. The process was repeated to remove the stratum corneum.

A punch biopsy is also taken, flash-frozen in liquid nitrogen and stored at −80° C. until analysis. Skin biopsy samples were homogenized and proteins were precipitated with acetonitrile. The extracts were filtered and the pharmacological drug compound in the test formulations was quantified by reversed phase HPLC. The amount of compound in the combined epidermal and dermal compartments is expressed as µg/g of skin (wet weight).

Figure 9:
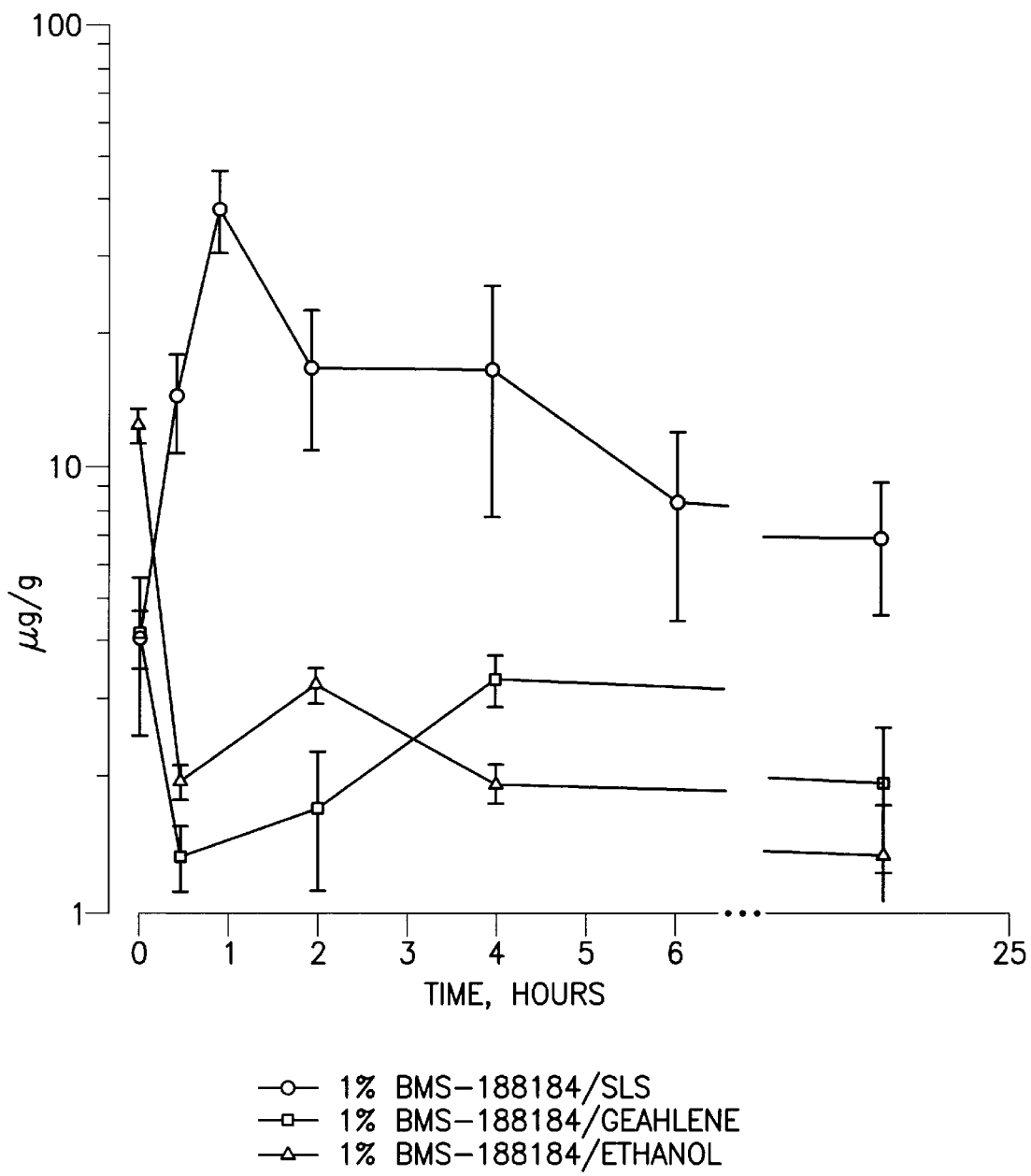
FIG. 9 depicts the results of in vivo skin retention assays using the hairless rat skin model system. The assays determined the skin retention ($\mu$g of drug per gram of skin) of phospholipase A2 inhibitor drug BMS-188184-02 from an active treatment composition comprising approximately 1%, w/w, of drug. In the dual system of the invention, the active treatment composition of 1% BMS-188184-02 was formed on the skin by mixing the ointment-based drug composition with cream permeation enhancer composition in a proportion of 1:1. (-●-: dual system active composition comprising BMS-188184-02, 2% ointment composition and 0.8% sodium lauryl sulfate (SLS) permeation enhancer cream composition); (-■-: active composition comprising BMS-188184-02, 1% mineral oil base ointment (GEAHLENE) composition); (-▲-: active composition comprising BMS-188184-02, 1% in ethanol solution as a permeation enhancer).
Figure 10:
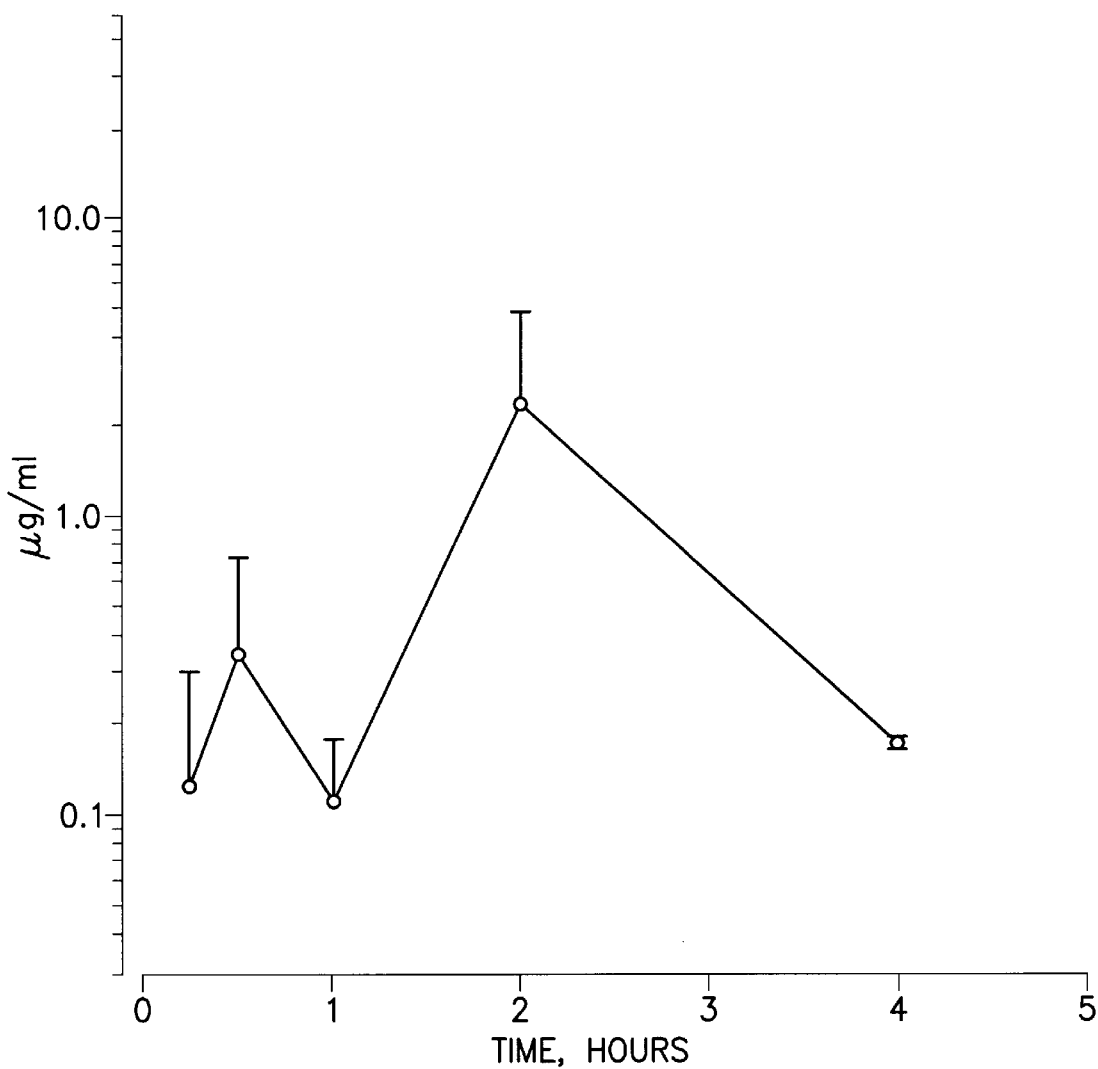
FIG. 10 shows the plasma concentration (in $\mu$g/mL) of BMS-188184-02 in hairless rats after a single topical dose of dual system 2% BMS-188184-02 ointment and SLS permeation enhancer cream compositions.

FIG. 9 shows the results of a comparison of the skin concentrations of BMS-188184-02 after topical application of test drug and permeation enhancer compositions delivered to the skin and combined on the site of application in accordance with a dual delivery system of the invention. In these experiments, the drug BMS-188184-02 was present in the ointment composition comprising drug in an amount of approximately 2%, w/w (Formulation 6, Table 4). Accordingly, after delivering and mixing the drug composition and the permeation enhancer composition on the skin, the drug was present at approximately 1% in the final active composition. In FIGS. 9 and 10, the filled circles represent a final active composition comprising approximately 1% drug and 0.4% sodium lauryl sulfate (SLS) as permeation enhancer; the filled squares represent a single phase composition comprising approximately 1% drug in GEAHLENE base formulation (Formulation 1, Table 1), which served as a control in these studies. The filled triangles represent a final active composition comprising approximately 1% drug in ethanol as permeation enhancer.

As can be seen by the results shown in FIG. 9, the active composition comprising a combination of drug and SLS and propylene glycol permeation enhancer significantly enhanced drug delivery to the skin, with peak skin concentrations occurring within one hour after application. At the two-hour time point, the final active composition comprising SLS as permeation enhancer delivered at least nine times more drug than the amount delivered by the control GEAHLENE base and drug formulation, and five times more drug than the amount delivered by the ethanol and drug formulation. These in vivo results in the hairless rat model are consistent with the results observed in the in vitro human skin penetration studies described in Example 4.

The concentrations of BMS-1881844-02 drug were also detected in plasma with peak plasma concentrations of 2.4 µg/mL at 2 hours (FIG. 10). The appearance of the drug in plasma confirmed the ability of the final composition, which resulted from dual delivery of drug and permeation enhancer to the skin and mixing same thereon, to deliver drug to the dermal layer where it was able to gain access to the vascular space. Blood levels of drug were not detected in the cases of one-component compositions comprising GEAHLENE base and a solution formulation containing ethanol as the permeation enhancing agents. By 6 hours after topical application, the concentration of drug in plasma was below the limit of detection. These data were consistent with the observation of greatly increased flux in in vitro skin penetration studies using human skin as described in Example 4.

Example 6

As presented in Table 8, dual systems with different permeation enhancers were compared with the single phase control comprising drug and GEAHLENE mineral oil formulation.

TABLE 8

1% BMS-188184 Active Ointment Composition Skin Permeation Summary

| FORMULA | Flux (μg/cm²-hr) | Skin Retention (μg/mg Skin) |
|---|---|---|
| GEAHLENE CONTROL FORMULA [# Subjects = 4/Each n = 2] | 0.17 (0.03)* | 0.45 (0.11)* |
| DUAL SYSTEM w/SLS [# Subjects = 4/Each n = 2] | 6.66 (1.33)* | 2.54 (0.32)* |
| DUAL SYSTEM w/DMS [# Subjects = 4/Each n = 2] | 4.55 (0.51)* | 2.22 (0.34)* |
| DUAL SYSTEM w/d-LIMONENE [# Subjects = 4/Each n = 2] | 4.05 (0.75)* | 2.82 (0.31)* |
| DUAL SYSTEM w/MENTHONE [# Subjects = 4/Each n = 2] | 2.85 (0.57)* | 3.54 (1.33)* |

*: Standard Error of Mean;
n = number of samples from each subject.

Figure 11:
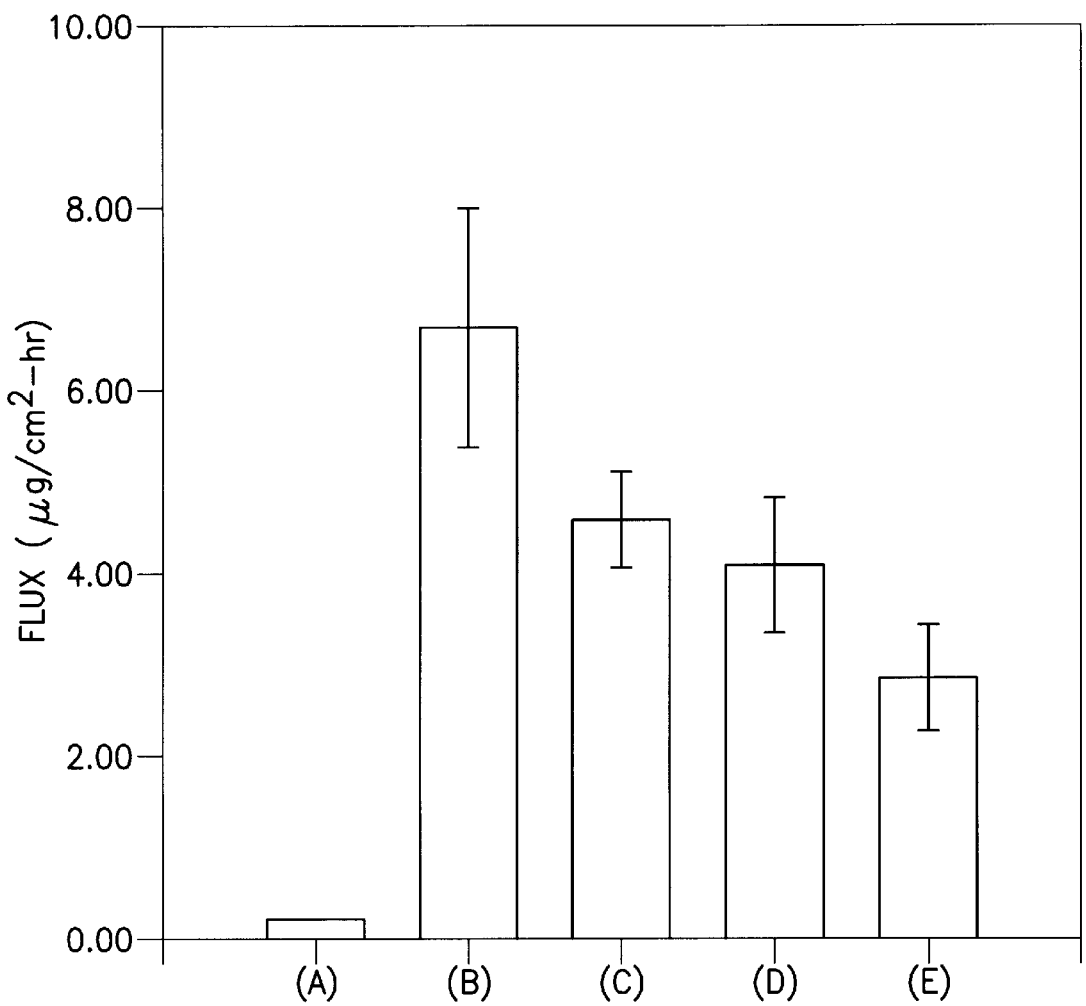
FIG. 11 depicts the results of in vitro skin penetration assays using the human cadaver skin model system in which flux was quantified. The assays determined the flux of phospholipase A2 inhibitor drug BMS-188184-02. In the dual system of the invention, an active treatment composition comprising approximately 1%, w/w, of drug was formed by mixing the ointment-based drug composition with various cream- or gel-based permeation enhancer compositions as described in Example 4, and compared with the GEAHLENE base ointment formulation as a control.

FIG. 11 shows the results of flux analyses using different gel or cream permeation enhancer compositions and the phospholipase A2 inhibitor drug composition in an ointment formulation. As described, this drug is unstable for long-term storage after mixing with the different permeation enhancers employed in the studies. In each of the final compositions, BMS-188184-02 drug was present at approximately 1%, w/w. [A] represents the results of the GEAHLENE (mineral oil) and drug composition used as control; [B] represents the results of a final active composition produced by mixing the drug ointment composition with a cream composition comprising 2% w/w propylene glycol with SLS as permeation enhancers, wherein SLS was present at approximately 0.4%, by weight, in the final composition; [C] represents the results of a final active composition produced by mixing the drug ointment composition with a cream composition comprising 2% w/w propylene glycol with decylmethylsulfoxide (DeMSO) as permeation enhancers, wherein DeMSO was present at approximately 1%, by weight, in the final composition; [D] represents the results of a final active composition produced by mixing the drug ointment composition with a cream composition comprising d-limonene as permeation enhancer, wherein d-limonene was present at approximately 2.5%, by weight, in the final composition; and [E] represents the results of a final active composition produced by mixing the drug ointment composition with a cream composition comprising menthone as permeation enhancer, wherein menthone was present at approximately 2.5%, by weight, in the final composition. Human cadaver skin from four subjects was used, with two replicates of each being assayed.

Figure 12:
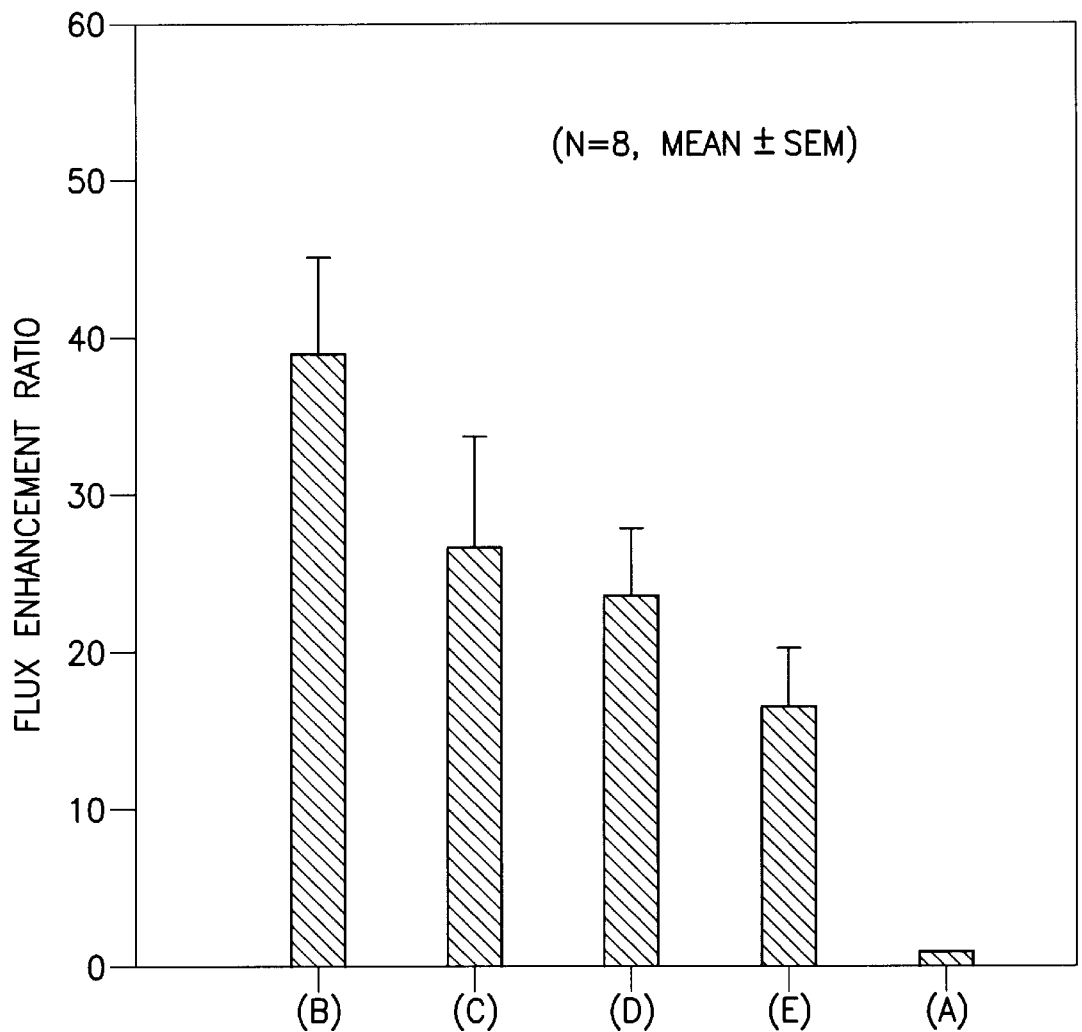
FIG. 12 shows enhancement ratios resulting from in vitro skin flux analyses of active treatment formulations comprising BMS-188184-02 and various permeation enhancers as described in Example 4, and compared with the GEAHLENE base ointment formulation as a control.
Figure 13:
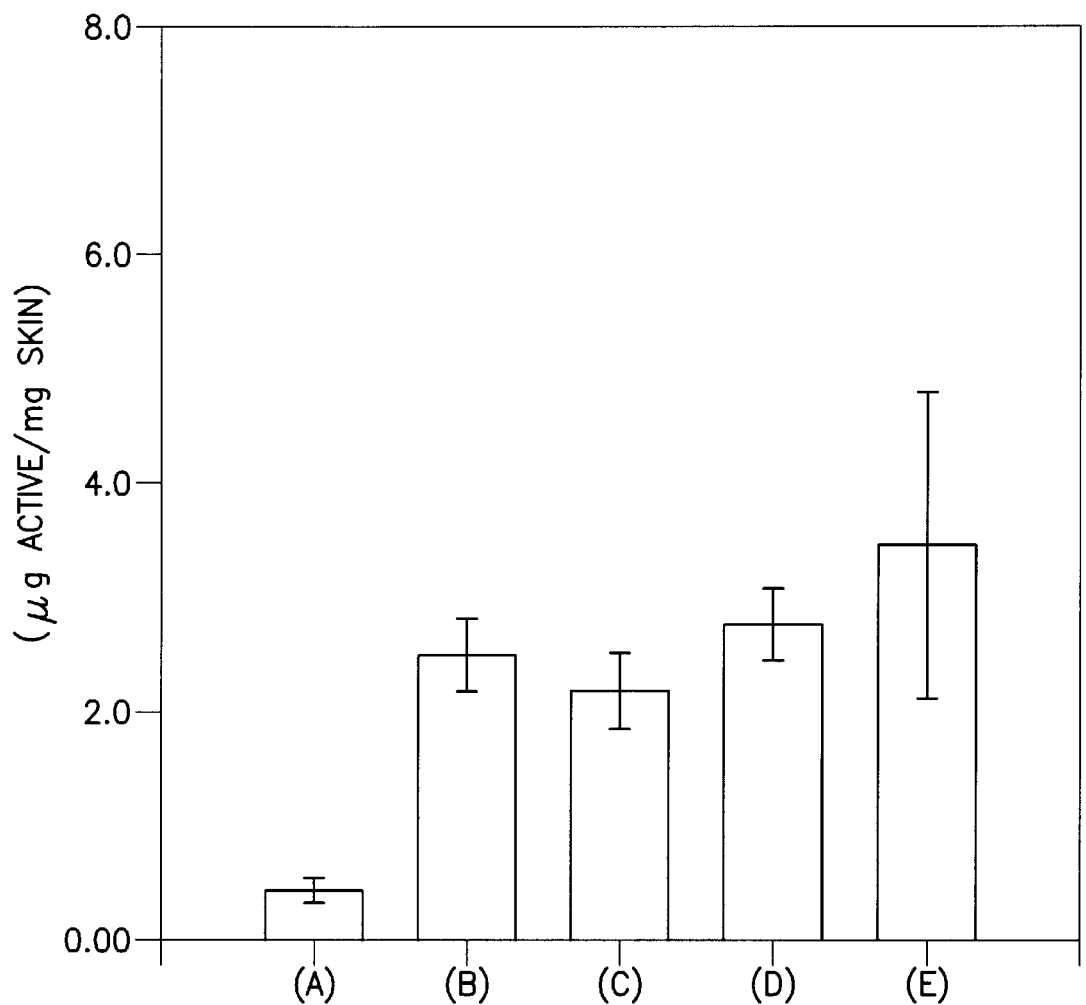
FIG. 13 depicts the results of in vitro skin penetration assays using the human cadaver skin model system. The assays determined the amount of skin retention ($\mu$g Active/ mg Skin) of phospholipase A2 inhibitor drug BMS-1881844-02 from an active treatment composition comprising approximately 1%, w/w, of drug. In the dual system, the active treatment composition was formed by mixing the ointment-based drug composition with various cream- or gel-based permeation enhancer compositions as described in Example 4, and compared with the GEAHLENE base ointment formulation as a control.

As presented in Table 8 and in FIGS. 11 and 12, relative to the GEAHLENE and drug control mixture, the greatest flux of drug through the skin was found using SLS as permeation enhancer in the active composition (i.e., 6.66 (1.33) μg/cm²-hr). This result demonstrates that SLS, which, under normal circumstances results in instability and degradation of the phospholipase A2 inhibitor with which it is combined during storage, was able to enhance the penetration of drug through the skin nearly 40-fold. The next most effective active composition comprised decylmethylsulfoxide as permeation enhancer; DMS enhanced the penetration of drug through the skin nearly 27-fold, relative to GEAHLENE control. The active composition comprising d-limonene as permeation enhancer enhanced the penetration of drug nearly 24-fold relative to control; and that comprising menthone enhanced the penetration of drug nearly 17-fold. FIG. 13 shows the amount of drug (μg) retained per mg of skin. In FIG. 8, the drug composition and permeation enhancer compositions [A]–[E] are identical to those described for FIG. 11.

Figure 14:
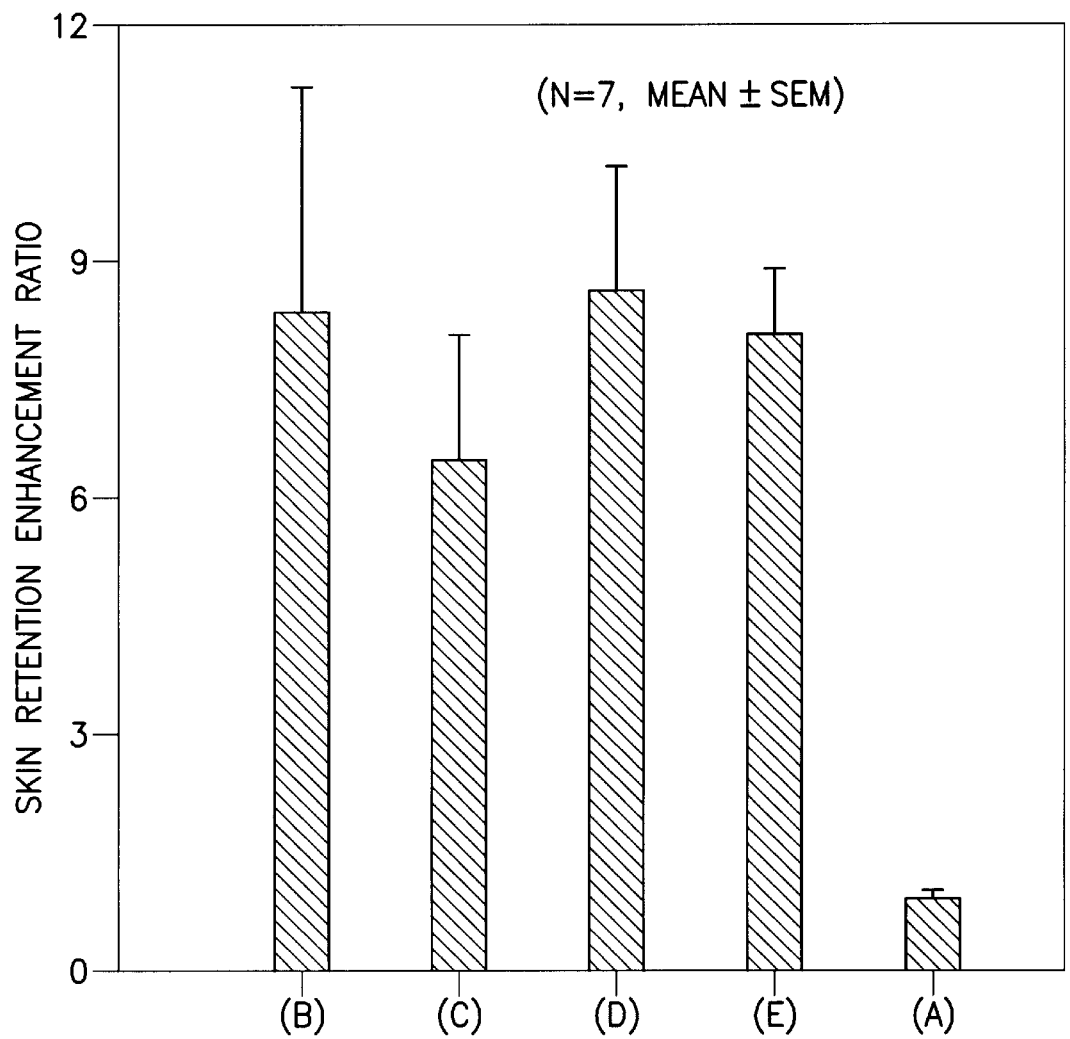
FIG. 14 shows enhancement ratios resulting from in vitro skin retention analyses of active treatment formulations comprising BMS-188184-02 and various permeation enhancers as described in Example 4, and compared with the GEAHLENE base ointment formulation as a control.

FIG. 14 shows the skin retention enhancement from the different dual system formulations described in Example 4. The skin retention enhancement of BMS-188184-02 was on the order of 5- to 7-fold higher from the dual system formulations containing permeation enhancers compared with the GEAHLENE formulation used as control.

The contents of all patents, patent applications, published articles, books, reference manuals and abstracts cited herein are hereby incorporated by reference in their entirety to more fully describe the state of the art to which the invention pertains.

As various changes can be made in the above-described subject matter without departing from the scope and spirit of the invention, it is intended that all subject matter contained in the above description, shown in the accompanying drawings, or defined in the appended claims will be interpreted as descriptive and illustrative, and not in a limiting sense. Many modifications and variations of the present invention are possible in light of the above teachings. It is therefore to be understood that within the scope of the appended claims, the invention may be practiced otherwise than as specifically described.

What is claimed is:

1. A process for enhancing skin permeation of a topically applied pharmacologically active compound which has a low rate of skin penetration, said process employing a permeation enhancer incompatible with said active compound, comprising:

a) preparing at least one first composition comprising the active compound and a pharmacologically acceptable vehicle for the active compound, the active compound having long-term storage stability in the vehicle and exhibiting a first rate of skin permeation when the first composition is applied to an area of skin, wherein the first rate of skin permeation is inadequate for the active compound to produce a desired effect;

b) preparing at least one second composition comprising a permeation enhancer for the active compound which is mixed with the active compound and applied to the same area of skin as the first composition of (a);

the active compound and the permeation enhancer being mutually incompatible, such that when mixed together and subjected to long-term storage, (i) the active compound produces one or more degradation byproducts, and/or ii) the permeation enhancer produces one or more degradation byproducts;

c) applying the first composition and the second composition to the same skin area, the first and second compositions being applied at the same time, successively, or as a premixture of the first and second compositions, provided that when the application is successive, one composition is applied within a short time after the other composition is applied, and when the application is of a premixture, the time elapsed between preparation of the premixture and application to the same skin area is such that the concentration of the active compound in the premixture is not less than a predetermined acceptable concentration;

whereby a second rate of skin permeation of the active compound is obtained, the second rate of skin permeation being substantially higher than the first rate, such that a therapeutically effective amount of the active compound is delivered, the desired effect is achieved, and formation of the degradation byproducts of the active compound and/or the permeation enhancer is substantially avoided.

2. The process according to claim 1, wherein the second rate is at least two-fold greater than the first rate.

3. The process according to claim 1, wherein the second rate is at least five-fold greater than the first rate.

4. The process according to claim 1, wherein the second rate is at least ten-fold greater than the first rate.

5. The process according to claim 1, wherein the second rate is at least fifty-fold greater than the first rate.

6. The process according to claim 1, wherein the second rate is at least two-fold to eighty-fold greater than the first rate.

7. The process according to claim 6, wherein the second rate is at least ten-fold to fifty-fold greater than the first rate.

8. The process according to claim 1, wherein the pharmacologically active compound is present in an amount of about 0.001 weight % to about 80 weight %, based on the weight of the active composition.

9. The process according to claim 1, wherein one composition is applied to said area within about one to thirty minutes after the other is applied to said area.

10. The process according to claim 9, wherein one composition is applied to said area within about five to ten minutes after the other is applied to said area.

11. The process according to claim 1, wherein one composition is applied to said area immediately after the other is applied thereto.

12. The process according to claim 1, wherein, when the premixture is applied, the time elapsed between the preparation of the premixture and the application to said area is less than about seven days.

13. The process according to claim 1, wherein the active compound is selected from the group consisting of steroidal anti-inflammatory compounds, nonsteroidal anti-inflammatory compounds, 5-lipoxygenase inhibitors, lipoxygenase inhibitors, cyclooxygenase inhibitors, phospholipase C inhibitors, phospholipase A2 inhibitors, protein kinase C inhibitors, interleukin-1 inhibitors, interleukin-1 receptor antagonists, 12-HETE inhibitors, imidazoles, retinoids, retinyl esters, PAF antagonists, essential fatty acids and analogues thereof, beta-2 agonists, beta-3 adrenergic receptor agonists, anti-pruritics, anti-bacterials, anti-fungals, anti-yeast compounds, antibiotics, antiseptics, anti-virals, anti-AIDS drugs, anti-ichthyosis drugs, drugs to treat disturbed or abnormal keratinization, anti-hyperpigmentation drugs, anti-psoriasis compounds, anti-acne compounds, anti-dandruff compounds, antihistamines, anti-plaque agents, local anesthetics, analgesics, beta-adrenoceptor blockers, β-blockers, broncho-spasm relaxants, anti-cancer agents, antianginal agents, vasodilators, anti-hypertensives, acetylcholinesterase inhibitors, anti-motion sickness agents, sex hormones, contraceptive agents, anti-asthma drugs, antitussives, vasodilators, anti-emetics, anticoagulants, decongestants, analgesics, antipyretics, anti-baldness/alopecia treatment agents, anti-dermatitis compounds, anti-ulcer drugs, antispasmodics, sympathomimetic amines, central nervous system active drugs, diuretics, anti-photoaging compounds, anti-UV compounds, vitamins and vitamin salts, protein drugs, peptide drugs, and mixtures or combinations thereof.

14. The process according to claim 13, wherein the active compound is a phospholipase A2 inhibitor.

15. The process according to claim 14, wherein the phospholipase A2 inhibitor is (2Z,4Z)-3-methyl-4-(3carboxyphenyl)-5-[(1,2,3,4-tetrahydro-1,1,4,4-tetramethyl)-6-anthracenyl]-2,4-pentadienoic acid.

16. The process according to claim 15, wherein the phospholipase A2 inhibitor is a di-potassium or a di-acid salt.

17. The process according to claim 1, wherein the second composition comprises a component selected from the group consisting of water, alcohols, propylene glycols, fatty alcohols, fatty acids, fatty acid esters, alkyl esters, polyols, sulfoxides, amides, surfactants, terpenes, alkanones, skin permeation enhancers and mixtures or combinations thereof.

18. The process according to claim 1 or claim 17, wherein the skin permeation enhancer is selected from the group consisting of sodium lauryl sulfate, dibutyl adipate, isopropylmyristate, dimethylsulfoxide, decylmethylsulfoxide, dimethylformamide, dimethylacetamide, glycerylmonocaprylate, propylene glycol, N-alkyl-2-pyrrolidone, d-limonene, menthone, ethanol, and mixtures or combinations thereof.

19. The process according to claim 14, claim 15 or claim 16, wherein the second composition comprises a component selected from the group consisting of water, alcohols, propylene glycols, fatty alcohols, fatty acids, fatty acid esters, alkyl esters, polyols, sulfoxides, amides, surfactants, terpenes, alkanones, skin permeation enhancers and mixtures or combinations thereof.

20. The process according to claim 19, wherein the second composition comprises a component selected from the group consisting of water, propylene glycol, ethyl alcohol, sodium lauryl sulfate, decylmethylsulfoxide, d-limonene, and menthone and mixtures or combinations thereof.

21. The process according to claim 20, wherein the rate of skin permeation of the phospholipase A2 inhibitor is increased or enhanced at least about two-fold when the first composition is combined with the second composition.

22. The process according to claim 20, wherein the rate of skin permeation of the phospholipase A2 inhibitor is increased or enhanced at least about five-fold when the first composition is combined with the second composition.

23. The process according to claim 20, wherein the rate of skin permeation of the phospholipase A2 inhibitor is increased or enhanced at least about ten-fold when the first composition is combined with the second composition.

24. The process according to claim 20, wherein the rate of skin permeation of the phospholipase A2 inhibitor is increased or enhanced at least about fifty-fold when the first composition is combined with the second composition.

25. The process according to claim 20, wherein the rate of skin permeation of the phospholipase A2 inhibitor is increased or enhanced at least about two-fold to eighty-fold when the first composition is combined with the second composition.

26. The process according to claim 25, wherein the rate of skin permeation of the phospholipase A2 inhibitor is increased or enhanced at least about ten-fold to fifty-fold greater than the first rate.

27. The process according to claim 1, wherein the application of degradation byproducts of the active compound and degradation byproducts of the permeation enhancer into the skin is substantially avoided.

28. The process according to claim 1, wherein the second composition comprising permeation enhancer is a solvent for the first composition comprising the active compound.

29. A compartmented device for enhancing penetration through the skin of a topically applied medicament which otherwise has a low rate of skin penetration and which is unstable for long-term storage when mixed with a permeation enhancing agent, said device having an upper surface unattached to the skin and a lower surface which adheres to the skin, comprising:

a first compartment housing at least one first composition comprising the medicament and a pharmacologically acceptable vehicle for the medicament, wherein the medicament has long-term stability in the vehicle, and further wherein the medicament has a first rate of penetration when the first composition is applied to an area of skin; and a second compartment, physically separated from the first compartment by a rupturable wall, which prevents contact between or diffusion of contents of the first and second compartments of the device, the second compartment housing at least one second composition comprising a penetration enhancing agent for the medicament, which is incompatible with the medicament in the first compartment and, when mixed with the medicament, results in instability and/or degradation of the medicament or instability and/or degradation of the permeation enhancing agent, such that long-term stability or storage of the medicament in the mixture is unattainable;

wherein, when pressure is applied to the upper surface of the device and the upper surface is vigorously rubbed, the wall separating the first and second compartments ruptures and the first medicament-containing composition mixes with the second penetration enhancer-containing composition to form an active treatment composition such that the first and the second compositions are applied to the same area of the skin; and further wherein, after mixing with the permeation enhancer and application to the skin, the medicament exhibits a second rate of skin penetration substantially higher than the first rate, and the long-term instability and/or degradation of the medicament with the permeation enhancer, and/or the long-term instability and/or degradation of the permeation enhancer with the medicament is substantially avoided.

30. The device according to claim 29, wherein said first and second compositions are simultaneously dispensed onto said area.

31. The device according to claim 29, wherein said active treatment composition is applied onto said area after the first and second compositions are mixed.

32. The device according to claim 31, wherein said active treatment composition is applied within about one to thirty minutes after the first and second compositions are mixed.

33. The device according to claim 32, wherein said active treatment composition is applied within about five to ten minutes after the first and second compositions are mixed.

34. The dispensing assembly according to claim 33, wherein the pharmacologically active compound is selected from the group consisting of steroidal anti-inflammatory compounds, nonsteroidal anti-inflammatory compounds, 5-lipoxygenase inhibitors, lipoxygenase inhibitors, cyclooxygenase inhibitors, phospholipase C inhibitors, phospholipase A2 inhibitors, protein kinase C inhibitors, interleukin-1 inhibitors, interleukin-1 receptor antagonists, 12-HETE inhibitors, imidazoles, retinoids, retinyl esters, PAF antagonists, essential fatty acids and analogues thereof, beta-2 agonists, beta-3 adrenergic receptor agonists, anti-pruritics, anti-bacterials, anti-fungals, anti-yeast compounds, antibiotics, antiseptics, anti-virals, anti-AIDS drugs, anti-ichthyosis drugs, drugs to treat disturbed or abnormal keratinization, anti-hyperpigmentation drugs, anti-psoriasis compounds, anti-acne compounds, anti-dandruff compounds, antihistamines, anti-plaque agents, local anesthetics, analgesics, beta-adrenoceptor blockers, β-blockers, broncho-spasm relaxants, anti-cancer agents, antianginal agents, vasodilators, anti-hypertensives, acetylcholinesterase inhibitors, anti-motion sickness agents, sex hormones, contraceptive agents, anti-asthma drugs, antitussives, vasodilators, anti-emetics, anti-coagulants, decongestants, analgesics, antipyretics, anti-baldness/alopecia treatment agents, anti-dermatitis compounds, anti-ulcer drugs, antispasmodics, sympathomimetic amines, central nervous system active drugs, diuretics, anti-photoaging compounds, anti-UV compounds, vitamins and vitamin salts, protein drugs, peptide drugs, and mixtures or combinations thereof.

35. The assembly according to claim 34, wherein the active compound in the first compartment is a phospholipase A2 inhibitor.

36. The assembly according to claim 35, wherein the phospholipase A2 inhibitor is (2Z,4Z)-3-methyl-4-(3carboxyphenyl)-5-[(1,2,3,4-tetrahydro-1,1,4,4-tetramethyl)-6-anthracenyl]-2,4-pentadienoic acid.

37. The assembly according to claim 36, wherein the phospholipase A2 inhibitor is a di-potassium or a di-acid salt.

38. The assembly according to claim 34, wherein the second composition in the second compartment comprises a component selected from the group consisting of water, alcohols, propylene glycols, fatty alcohols, fatty acids, fatty acid esters, alkyl esters, polyols, sulfoxides, amides, surfactants, terpenes, alkanones, skin permeation enhancers and mixtures or combinations thereof.

39. The assembly according to claim 38, wherein the skin permeation enhancer is selected from the group consisting of sodium lauryl sulfate, dibutyl adipate, isopropylmyristate, dimethylsulfoxide, decylmethylsulfoxide, dimethylformamide, dimethylacetamide, glycerylmonocaprylate, propylene glycol, N-alkyl-2-pyrrolidone, d-limonene, menthone, ethanol, and mixtures or combinations thereof.

40. The assembly according to any of claims 35, 36 or 37, wherein the second composition comprises a component selected from the group consisting of water, propylene glycol, ethyl alcohol, sodium lauryl sulfate, decylmethylsulfoxide, d-limonene, and menthone and mixtures or combinations thereof.

41. The assembly according to claim 35, wherein the rate of skin permeation of the phospholipase A2 inhibitor is increased or enhanced at least about two-fold when the first composition is combined with the second composition.

42. The assembly according to claim 35, wherein the rate of skin permeation of the phospholipase A2 inhibitor is increased or enhanced at least about five-fold when the first composition is combined with the second composition.

43. The assembly according to claim 35, wherein the rate of skin permeation of the phospholipase A2 inhibitor is increased or enhanced at least about ten-fold when the first composition is combined with the second composition.

44. The assembly according to claim 35, wherein the rate of skin permeation of the phospholipase A2 inhibitor is increased or enhanced at least about fifty-fold when the first composition is combined with the second composition.

45. The assembly according to claim 35, wherein the rate of skin permeation of the phospholipase A2 inhibitor is increased or enhanced about two-fold to about eighty-fold when the first composition is combined with the second composition.

46. A dispensing assembly for enhancing skin penetration of a topically applied pharmacologically active compound, the active compound exhibiting a first low rate of skin permeation when applied to an area of skin and being incompatible with a permeation enhancer which enhances skin penetration, comprising:

a) a first compartment comprising at least one first composition comprising the active compound and a pharmaceutically acceptable vehicle for the compound, the active compound having long-term storage stability in the vehicle and having a first rate of skin permeation when the first composition is applied to an area of skin, the first rate of skin permeation being inadequate for the active compound to produce a desired effect;

b) a second compartment comprising at least one second composition comprising the permeation enhancer for the active compound which is mixed with the active compound and applied to the same area of skin as the first composition of (a);

the active compound and the permeation enhancer being mutually incompatible, such that when mixed together and subjected to long-term storage, (i) the active compound produces one or more degradation byproducts, and/or ii) the permeation enhancer produces one or more degradation byproducts;

c) means for simultaneously delivering doses of the separated first and second compositions from their respective first and second compartments onto the same area of skin so that mixing at the time of application is facilitated; wherein the delivery of the doses of the first and second compositions on the skin area forms an active composition comprising the active compound, the vehicle, and the permeation enhancer, thereby resulting in a second rate of skin permeation of the active compound, the second rate of skin permeation being substantially higher than the first rate, such that a therapeutically effective amount of the active compound is delivered and the desired effect is achieved; and further wherein the formation of the degradation byproducts of the active compound and/or the permeation enhancer is substantially avoided.

* * * * *